US008886280B2

(12) United States Patent
Kartush

(10) Patent No.: US 8,886,280 B2
(45) Date of Patent: Nov. 11, 2014

(54) NERVE MONITORING DEVICE

(75) Inventor: Jack M. Kartush, Bloomfield Hills, MI (US)

(73) Assignee: The Magstim Company Limited, Whitland, Dyfed (GB)

( * ) Notice: Subject to any disclaimer, the term of this patent is extended or adjusted under 35 U.S.C. 154(b) by 191 days.

(21) Appl. No.: 12/851,300

(22) Filed: Aug. 5, 2010

(65) Prior Publication Data

US 2010/0317956 A1 Dec. 16, 2010

Related U.S. Application Data

(63) Continuation-in-part of application No. 12/704,303, filed on Feb. 11, 2010, which is a continuation-in-part of application No. 12/523,931, filed as application No. PCT/US2008/051768 on Jan. 23, 2008.

(60) Provisional application No. 60/886,119, filed on Jan. 23, 2007, provisional application No. 61/151,943, filed on Feb. 12, 2009.

(51) Int. Cl.
*A61B 5/04* (2006.01)
*A61B 5/00* (2006.01)
*A61N 1/36* (2006.01)
*A61N 1/05* (2006.01)
*A61B 5/0488* (2006.01)
*A61B 18/18* (2006.01)
*A61B 19/00* (2006.01)
*A61M 16/04* (2006.01)
*A61B 1/267* (2006.01)

(52) U.S. Cl.
CPC .......... *A61B 5/04886* (2013.01); *A61B 5/6853* (2013.01); *A61B 5/6859* (2013.01); *A61B 5/6886* (2013.01); *A61B 5/04001* (2013.01); *A61B 5/6885* (2013.01); *A61M 2205/581* (2013.01); *A61M 16/0434* (2013.01); *A61N 1/3606* (2013.01); *A61M 16/0488* (2013.01); *A61M 2230/60* (2013.01); *A61B 5/6858* (2013.01); *A61N 1/0519* (2013.01); *A61M 2205/18* (2013.01); *A61B 1/267* (2013.01); *A61M 2205/583* (2013.01); *A61M 2205/3592* (2013.01); *A61M 2205/584* (2013.01); *A61M 16/04* (2013.01); *A61M 2205/3561* (2013.01)
USPC .............. 600/380; 600/546; 606/46; 606/129

(58) Field of Classification Search
CPC ................ A61B 5/04; A61B 5/04001; A61B 5/046885; A61B 5/04886; A61B 5/6858; A61B 5/6886; A61M 16/0488; A61M 2230/60
USPC ......... 600/372–373, 380, 393, 466, 470, 546; 606/32, 46–47; 607/40, 42, 44, 72
See application file for complete search history.

(56) References Cited

U.S. PATENT DOCUMENTS 4,567,882 A 2/1986 Heller
4,960,122 A 10/1990 Mizus
(Continued)

FOREIGN PATENT DOCUMENTS

WO 9324170 12/1993

OTHER PUBLICATIONS

European Search Report, European Patent Application No. 10157120.6, Aug. 27, 2010.

(Continued)

*Primary Examiner* — Linda Dvorak
*Assistant Examiner* — Brian M Antiskay
(74) *Attorney, Agent, or Firm* — Troutman Sanders LLP; Ryan A. Schneider; Troy S. Kleckley

(57) ABSTRACT

A nerve monitoring device, including a cannula, a sensor for monitoring a nerve, and an optional support element, can be inserted into an anatomic space. The cannula, sensor and/or support element can automatically conform to and match the geometry of the anatomic space, which can enhance desired contact between the sensor and anatomic features, such as muscles, nerves or tissue in the space in an atraumatic manner. The sensor, cannula and/or support element can include one or more strips or other elements that convert from a retracted mode to an expanded mode in which the strips or elements expand, enlarge or otherwise move to match the geometry of the space and place the sensors in precise monitoring proximity relative to the target muscles, nerves or tissues. An exemplary application of the device is in the field of laryngeal monitoring, however, the device is well suited for other applications.

16 Claims, 13 Drawing Sheets

(56) References Cited

U.S. PATENT DOCUMENTS

| | | | |
|---|---|---|---|
| 4,976,261 | A | 12/1990 | Gluck et al. |
| 5,016,647 | A | 5/1991 | Sanders |
| 5,125,406 | A | 6/1992 | Goldstone et al. |
| 5,135,001 | A * | 8/1992 | Sinofsky et al. ............. 600/459 |
| 5,178,145 | A | 1/1993 | Rea |
| 5,499,625 | A | 3/1996 | Frass et al. |
| 6,036,687 | A * | 3/2000 | Laufer et al. .................... 606/27 |
| 6,142,993 | A * | 11/2000 | Whayne et al. ................. 606/41 |
| 6,161,537 | A | 12/2000 | Gravenstein et al. |
| 6,173,199 | B1 | 1/2001 | Gabriel |
| 6,216,696 | B1 | 4/2001 | van den Berg |
| 6,266,548 | B1 | 7/2001 | Lamade et al. |
| 6,292,701 | B1 | 9/2001 | Prass et al. |
| 6,334,068 | B1 | 12/2001 | Hacker |
| 6,651,665 | B1 | 11/2003 | Sellers et al. |
| 6,701,918 | B2 | 3/2004 | Fariss et al. |
| 6,715,491 | B2 | 4/2004 | Cooper et al. |
| 6,735,471 | B2 | 5/2004 | Hill et al. |
| 7,216,001 | B2 | 5/2007 | Hacker et al. |
| 7,543,586 | B2 | 6/2009 | Qureshi et al. |
| RE41,334 | E | 5/2010 | Beatty et al. |
| 2005/0085743 | A1 | 4/2005 | Hacker et al. |
| 2006/0147492 | A1 | 7/2006 | Hunter et al. |
| 2006/0190053 | A1 | 8/2006 | Dobak, III |
| 2007/0016097 | A1 | 1/2007 | Farquhar et al. |
| 2007/0073160 | A1 | 3/2007 | Imam |
| 2007/0137652 | A1 | 6/2007 | Qureshi et al. |
| 2010/0179417 | A1 | 7/2010 | Russo |

OTHER PUBLICATIONS

International Search Report, International Application No. PCT/US2008/051768, Jul. 30, 2008.

Written Opinion of the International Searching Authority, International Application No. PCT/US2008/051768, Jul. 30, 2008.

Kartush, JM, Electroneurography and Intraoperative Facial Monitoring in Contemporary Neurotology; Otolaryngology-Head and Neck Surgery, vol. 101, No. 4, pp. 496-503, Oct. 1989.

Kartush, J, et al, Facial nerve testing; ENoG and intraoperative monitoring, J. Johnson (ed.), Mosby, 1988.

Kartush, JM, et al, Intraoperative Facial Nerve Monitoring: A Comparison of Stimulating Electrodes; Laryngoscope, vol. 95, pp. 1536-1540, Dec. 1985.

Kartush, JM, et al, Facial Nerve Outcome in Acoustic Neuroma Surgery, Otolaryngologic Clinics of North America, vol. 25, No. 3, pp. 623-647, Jun. 1992.

Kartush, JM, et al, Intraoperative Facial Nerve Monitoring: Otology, Neurotology and Skull Base Surgery, Neuromonitoring in Otology and Head and Neck Surgery, J.M. Kartush, K.R. Bouchard (eds.), Raven Press, New York, ch. 5, pp. 99-120, 1992.

Kartush, JM, et al, Acoustic Neuroma Update, Otolaryngologic Clinics of North America, Jack M. Kartush, MD (ed.), W.B. Saunders, Philadelphia, vol. 29, No. 3, Jun. 1996.

Witt, Robert L., Recurrent Laryngeal Nerve Electrophysiologic Monitoring in Thyroid Surgery: The Standard of Care?, Journal of Voice, vol. 19, Issue 3, pp. 497-500, Sep. 2005.

Kartush, JM et al, Facial Electroneurography: Clinical and experimental investigations; Otolaryngology-Head and Neck Surgery, vol. 93, No. 5, pp. 516-523, Aug. 1985.

* cited by examiner

NERVE MONITORING DEVICE

This application is a continuation-in-part of U.S. application Ser. No. 12/704,303, filed Feb. 11, 2010, which (a) is a continuation-in-part of U.S. application Ser. No. 12/523,931, filed Jul. 21, 2009, which is the National Stage of PCT/US08/51768, filed Jan. 23, 2008, and which claims priority benefit to U.S. Provisional Application 60/886,119, filed Jan. 23, 2007, and (b) also claims priority benefit to U.S. Provisional Application 61/151,943, filed Feb. 12, 2009. All of the foregoing are hereby incorporated by reference.

BACKGROUND OF THE INVENTION

The present invention relates to nerve monitoring, and more particularly, to a device to facilitate nerve monitoring.

A risk presented by thyroid surgery, parathyroid surgery, skull base surgery, cervical spine, or any other surgery in the space around the oropharynx, larynx, trachea or esophagus, is damage to the Recurrent Laryngeal Nerves ("RLN"). RLNs control the vocal cords, and damage to them can result in full or partial vocal cord paralysis. An issue with RLNs is that they are small and difficult to identify, particularly where surrounding tissue is bloodied, inflamed or otherwise disrupted due to surgery or trauma. Another issue is that simply trying to identify RLNs by touch can stretch or tear those nerves, which can result in hoarseness, difficulty in speech, aspiration of food or liquids (which can result in pneumonia), and life-threatening airway obstruction.

Accordingly, there have been recent efforts to use intraoperative RLN monitoring techniques, with the objective of reducing the risk of damage to the RLNs and subsequent vocal cord impairment or paralysis. One advocated form of RLN monitoring implements electromyography (EMG) to protect the nerves.

A common procedure in which laryngeal EMG is used is a thyroid surgery. In this procedure, a specialized endotracheal tube (ET tube) is placed through the patient's nose or mouth and into the trachea to assist in respiratory ventilation and/or to provide anesthesia. The ET tube also passes between the sets of laryngeal muscles, and typically rests adjacent the left and right posterior cricoarytenoid muscles. The specialized ET tube includes a pair of exposed, cylindrical wires on its external surface or embedded therein. These wires form electrodes that are intended to contact the various vocal muscles when the ET tube is (a) properly inserted at the correct depth, and (b) properly rotationally oriented relative to the trachea and larynx. These electrodes of the ET tube are capable of detecting EMG signals generated by an electrical probe. An example of such a specialized tube is disclosed in U.S. Pat. No. 5,125,406 to Goldstone, which is hereby incorporated by reference.

During the procedure, a surgeon applies the electrical probe to the area in which he believes the RLN is located. If the electrical probe applies voltage to or near the RLN, the electrical pulse is carried to the vocal muscles (primarily the "thyroarytenoid muscles" along the vocal cords anteriorly and the "posterior cricoarytenoid muscles" posteriorly) through the RLN, which in turn causes contraction of the vocal muscles which generate their own electric pulse. The respective wire electrode on the ET tube facing the stimulated vocal muscles subsequently detects the electromyographic (EMG) response. The detecting electrode transfers a signal to a receiver or EMG monitor, which emits an audio or visual alarm. This output alerts the surgeon that the probe is close to the RLN so that the surgeon can confirm the nerve's location and minimize trauma in the probed location.

One commercially available instrument suitable for the above procedure is the Kartush Stimulating Dissection Instruments (KSD), which allow ongoing electrical mapping of the nerve's location during surgical dissection by simultaneous stimulation and surgical dissection. Education, however, is required of thyroid and other surgeons using the above procedure to assure appropriate Stimulating Dissection to minimize false positive and false negative stimulation errors.

Another challenge concerning the above procedure concerns minimizing false negative and positive recording errors, especially related to contact between the electrodes on the ET tube and the laryngeal muscles to monitor the RLN. It is frequently difficult to ensure adequate Electrode-Vocal Cord (EVC) contact both as the ET tube is being inserted in the patient and after the ET tube is positioned. In other words, the ET tube electrodes used to monitor the RLN can be difficult to accurately place, as well as difficult to maintain in proper position.

Obtaining sufficient EVC contact is limited by several factors. First, direct visualization of the EVC juxtaposition typically occurs only during intubation. Even if the ET tube is checked immediately after positioning in the patient, loss of appropriate EVC contact may go undetected if it is not repeatedly checked. Further, the anterior location of the larynx or a large, floppy epiglottis can prevent direct visualization of EVC contact, even with a laryngoscope. Although this can be overcome by a flexible scope, the time and expense to add intermittent or ongoing flexible fiber optic endoscopy following standard intubation with a rigid laryngoscope can make this procedure impractical.

Second, the electrodes of the current and previous devices are positioned on a round ET tube, however, the aperture of the human glottis, i.e., the glottic opening, is triangular. This creates a fundamental mismatch between the geometry of the ET tube and the laryngeal surfaces, such as the glottic opening and other surrounding laryngeal muscles. An example of a conventional ET tube 1, including conventional wire electrodes 3, is shown in FIG. 1. As can be seen there, the ET tube 1 is circular, while the glottic opening 2 is generally triangular, which results in a mismatch between the ET tube and the laryngeal anatomical geometrics, and subsequently contact with the target laryngeal muscles. There have been attempts to improve electrode contact by simply increasing the outer diameter of standard ET tubes to press the electrode on the target laryngeal muscles, which may be the vocal cords. These attempts, however, can lead to difficult and traumatic intubations, as well as the possibility of pressure-induced vocal cord injury, particularly during prolonged operations such as removal of skull base tumors.

Third, there can be anatomic variances in the pharynx and larynx that can force the ET tube to enter the glottis at an angle that reduces contact at the EVC interface, that is, the ET tube may be placed too anterior or too posterior to the laryngeal muscles. An example of the ET tube 1 being placed too anterior (see arrow) to the posterior criciarytenoid muscles 4 so that the electrodes 3 do not have adequate contact with these target muscles 4 is illustrated in FIG. 2. Further, The ET tube may be inserted too deeply or too shallow, which can result in the electrodes being placed inferior or superior to the laryngeal muscles.

Fourth, inadvertent rotation of the ET tube about its longitudinal axis can skew the electrodes away from the target laryngeal muscles and minimize or eliminate proper contact. For example, as shown in FIG. 1, the electrodes 3 have been inadvertently placed opposite the target laryngeal muscles 4, thereby eliminating contact with those target muscles 4.

Without contact between the electrodes and the vocal cords, the device may provide a "false negative error"—that is, the device might not emit an alarm indicating detection of the electrical impulse in the muscle. Thus, the surgeon may not appreciate the proximity of the RLN to the electrical probe. Rotation issues may also be exacerbated by a recent shift toward the use of a more rigid, reinforced ET tube (intended to make intubation easier). With this construction, minor rotation of the ET tube at the mouth can result in rotation at the vocal cords or generally within the laryngeal space.

Fifth, to compensate for inaccurate ET tube insertion depth, some ET tubes have increased the un-insulated contact area of the electrodes. This modification, however, can increase the possibility of a "false positive error." For example, increased exposure of the tube's electrodes can detect inferior constrictor muscle activity. This inadvertently detected stimulation of the inferior constrictor muscle may be misinterpreted as vocal cord stimulation and proximity to the RLN by the electrical probe. Such false positive errors can lead to considerable anatomic disorientation of the surgeon.

Sixth, the EVC contact interface can dry over prolonged periods of contact. This drying can increase impedance which can reduce the detection of the EMG response. In a similar manner, too much moisture from secretions or intentionally applied lubricating jelly may cause shunting of the electrical response away from the electrodes, thereby reducing EVC contact.

Seventh, both false positive and false negative errors can be caused by improperly set coding parameters between the electrodes and the alarm monitor. For example, if the stimulus filter (Ignore Period) is set too long by a surgeon, it may filter out both the true response as well as the stimulus artifact.

Accordingly, there remains room for improving nerve monitoring devices to ensure that the monitored nerves are not damaged or impaired due to inadvertent contact or severing.

SUMMARY OF THE INVENTION

A nerve monitoring device and related method are provided to efficiently monitor a variety of nerves within a subject's body.

In one embodiment, the device can include a cannula and a sensor for monitoring a nerve. The device can be inserted into a body space at a desired depth of insertion and at a desired rotational orientation to monitor the activity of the nerve and/or an associated muscle(s).

In another embodiment, the sensor can be in communication with a processor to which the sensor outputs signals or data concerning electrical stimulation of the nerve and/or associated muscle caused by an electrical probe in electrical communication with the sensor. The processor can analyze the output of the sensor and can provide information to a health care provider, for example, a surgeon or nurse, concerning the nerve activity. This information can be indicative of the location of the nerve relative to the electrical probe, and can be output in the form of visual and/or audible output to the health care provider.

In yet another embodiment, the sensor can include structural elements that enhance contact between the sensor with the anatomic features, such as muscles, nerves or tissue, within a body space in which the cannula is inserted in an atraumatic manner. Optionally, the sensor can be of a geometric configuration that moves to conform to the geometric configuration of the body space within which the cannula is placed so that the sensors satisfactorily contact the target muscle and/or nerve.

In still yet another embodiment, where the device includes the cannula and sensor to enhance contact between the sensor and the anatomical features, the sensor can include electrodes that are moveable, flexible, compressible and/or expandable. For example, the electrodes can be constructed from a soft, felt-like material, or some other flexible or expandable or compressible material or elements. With such a sensor, even where the cannula is geometrically dissimilar to the body space within which it is placed, the electrodes joined with the cannula can overcome this mismatch, and satisfactorily contact the target muscle(s) and/or nerve to monitor the nerve. Optionally, the sensor and/or cannula can be constructed to be self-positioning and self-mobilizing, such that the elements of the sensor engage the geometric space into which the device is positioned, and automatically orient the sensor and/or the cannula appropriately within the anatomic space, or at least provide feedback to the health care provider to assist them in orientation. Such a construction can facilitate precise and appropriate atraumatic positioning relative to the surrounding geometry of the respective anatomic space.

In even another embodiment, where the device includes the cannula and sensor to enhance contact between the sensor and the anatomical features, the sensor can be in the form of a multi-electrode array, having multiple electrodes positioned around the cannula in a predetermined configuration. This array of electrodes can compensate for any rotational error of the cannula within the body space relative to the target muscle(s)/nerve. This embodiment goes beyond standard monopolar or bipolar electrodes by allowing complete user selection of whichever electrode combination provides clinically the most useful montage.

In another, further embodiment, where the device includes the cannula and sensor to enhance contact between the sensor and the anatomical features, the device or cannula can further include a support element which, when placed in the body space, expands to substantially fill at least a cross section of the body space. The electrodes can be joined with the surface of the support element and configured so that they move and/or reorient relative to the body space. Where the support element expands sufficiently so that the surface engages a target muscle(s) or nerve within the body space, the sensor likewise can contact the muscle(s) and/or nerve to monitor the nerve.

In another, additional embodiment, where the device includes the cannula sensor and support element, the support element can be constructed from a material having sponge-like properties, that is, it expands when wetted. The sensor can include electrodes connected to sensory elements, such as caps, located on or adjacent the surface of the support element. The sensor elements can move from a position proximal the cannula, to a position distal from the cannula, and adjacent a target nerve and/or muscle(s), when the expanding element is activated, for example, when it is wetted.

In yet another, additional embodiment, where the device includes the cannula, sensor and support element, the support element can include a plurality of elongated members, also referred to as strips, attached to a first end. The strips can be moveable, and in some cases bendable, outwardly from the cannula so that one or more of the strips conform to the body space in which the device is positioned. The strips of the support element can include sensors joined with them so that those sensors can contact target muscles and/or nerves in the body space. Alternatively, the sensor or electrodes can be built into the support element so that the strips themselves have sensing capabilities, or the support element can be absent altogether, with the sensor constructed to include the above noted strips.

In still another embodiment, the cannula, support element and/or sensor can be constructed to be self-positioning and self-mobilizing, such that the elements of the same engage the geometric space into which the device is positioned, and automatically orient the sensor, support element and/or the cannula appropriately within the anatomic space, or at least provide feedback to the health care provider to assist them in orientation. Such a construction can facilitate precise and appropriate atraumatic positioning relative to the surrounding geometry of the respective anatomic space.

In still yet another, additional embodiment, where the device includes the cannula, sensor and support element, the strips can include an actuator to engage the strips and/or the first end and urge them to move outwardly relative to the cannula. The actuator can include a manually operable handle, or an automated actuator that is remotely operable by the user.

In a further embodiment, where the device includes the cannula and sensor to enhance contact between the sensor and the anatomical features, the cannula can be constructed so that its external geometry is conformable to the body space within which it and the sensor is placed. For example, the cannula can be constructed to include, or joined with a support element constructed from, a material that selectively and atraumatically expands or compresses or otherwise changes in shape, or moves an exterior surface of the cannula. In turn, the exterior surface of the cannula generally conforms to the anatomic geometry of a body space with which the cannula is positioned. In its altered configuration, the cannula or support element constructed from the above material can urge and/or maintain the sensor, which is attached adjacent the conforming material, into contact with the target nerve/muscle(s) to ensure appropriate monitoring.

In still a further embodiment, where the device includes the cannula and sensor to enhance contact between the sensor and the anatomical features, the cannula can include a cannula wall of a thickness sufficient to enable the wall to flex and/or deform when positioned in a body space adjacent a target muscle and/or nerve. Optionally, the cannula wall can be constructed of a compliant, flexible material that reactively alters the geometric cross section of the cannula when the cannula is placed in a body space adjacent a target muscle/ nerve. As an example, the cannula can include walls constructed from a polymeric material and of a thickness that enables the wall(s) to flex or deform under forces encountered when a cannula is inserted in an internal body space. Optionally, the cannula can be an ET tube, adapted for insertion into a laryngeal space. The wall(s) of the ET tube, when positioned through the generally triangular laryngeal space, can flex and change shape so that the wall(s) become generally triangular, conforming to the triangular laryngeal space, such as the glottis. A sensor joined with a surface of the cannula can be urged into contact with the muscles and/or nerves in laryngeal space. The generally automatically conforming cannula can enhance the contact of the sensor, for example, an electrode, with the target muscle(s) and/or nerve, for example, one or more laryngeal muscles, to properly monitor the nerve(s).

In still yet a further embodiment, the device can include a cannula, an optional sensor for monitoring a target nerve/ muscle(s) and an alignment element. The cannula can be any surgical cannula, for example, an ET tube. The sensor can be an electrode or other sensor that is capable of sensing nerve or muscle activity. The alignment element can be configured and can include an indicator element that assists in ensuring that after insertion of the sensor into an internal body space of a patient, the sensor is aligned with the target nerve or muscle.

The indicator element can output signals or information externally, through body tissue, for example, transcutaneously, to a health care provider. The signals optionally can convey information regarding the insertion depth of the ET tube, as well as rotational alignment of features of the ET tube and/or sensors relative to a target nerve/muscle(s). The indicator element may act as either transmitter or receiver.

In an even further embodiment, the device including the cannula, the sensor and the alignment element can be configured with the alignment element joined in a fixed relationship to the cannula. The alignment element can include at least one alignment indicator that provides visual, aural or other signaling output to a health care provider to convey information concerning the rotational orientation of the cannula relative to the space and/or the depth of the cannula into the body space. Optionally, the alignment indicator can include elements that light in a manner that is visible exteriorly to the body in which the device is placed. Further optionally, the alignment indicator can be or include a transmitter and/or receiver that communicates with a corresponding device placed externally in relation to the body space.

In still another, further embodiment, the device including the cannula, the optional sensor and the alignment element can include multiple alignment indicators corresponding to different portions of the cannula. Optionally, the sensor can include one or more electrodes configured and oriented in a predetermined spatial relationship relative to the cannula and/ or the alignment element. The electrodes can be configured to contact and measure the response (if any) of a muscle/nerve within the body space where a nerve associated with the muscle is electrically stimulated, for example, by a stimulating probe. In one exemplary context, where an ET tube includes a cuff and an insertion tip, the alignment indicator can include a first alignment indicator joined with the insertion tip of the ET tube, another adjacent and below the cuff, and another adjacent but above the cuff. The indicators can illuminate or otherwise provide output through the tissue of the neck that a health care provider can visually or otherwise perceive and assess the location of these indicators, and thus the different parts of the ET tube, in the laryngeal space. If the health care provider perceives that the alignment indicators are out of their proper location, for example, the ET tube tip indicator is not far enough in the trachea, or an alignment indicator is rotated relative to a preferred location, the health care provider can take corrective action and reorient the ET tube to an appropriate orientation and/or position within the laryngeal space.

The device described herein provides a simple and efficient construction for atraumatically positioning and optionally maintaining a cannula within unique anatomical geometries of an internal body space. The device can provide reliable contact between sensors associated with the cannula and target muscles/nerves. Accordingly, the associated nerve and its location can be readily and reliably ascertained by a health care provider. This can prevent undesirable damage to or impairment of the nerve, particularly during surgery in a location near the nerve. Further, where an alignment element is included, the device can enhance measurement of stimulated muscles/nerves by generally enhancing sensor placement and/or cannula placement. Where an alignment element is associated with the cannula, that element can enhance proper placement and rotational orientation of the cannula within the respective body space.

These and other objects, advantages and features of the invention will be more fully understood and appreciated by reference to the description of the current embodiment and the drawings.

DESCRIPTION OF THE CURRENT EMBODIMENTS

Figure 1:
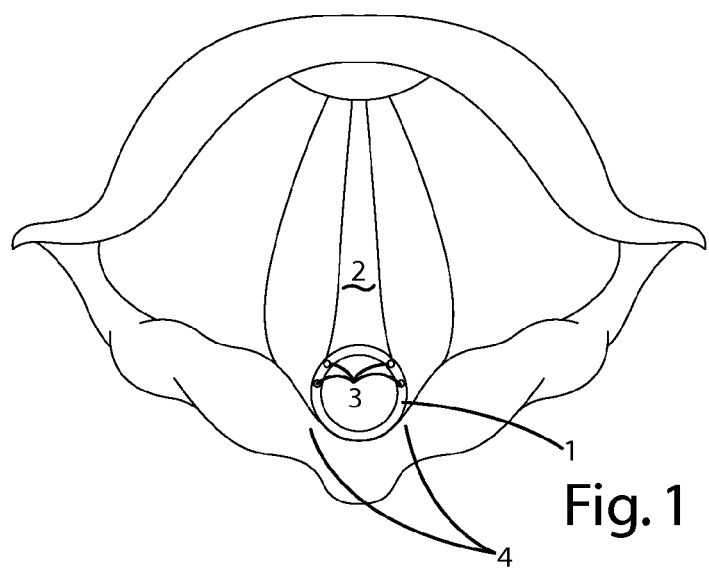
FIG. 1 is a top view of a prior art endotracheal tube including electrodes that are improperly positioned within the glottic opening, and out of contact with posterior target muscles.
Figure 2:
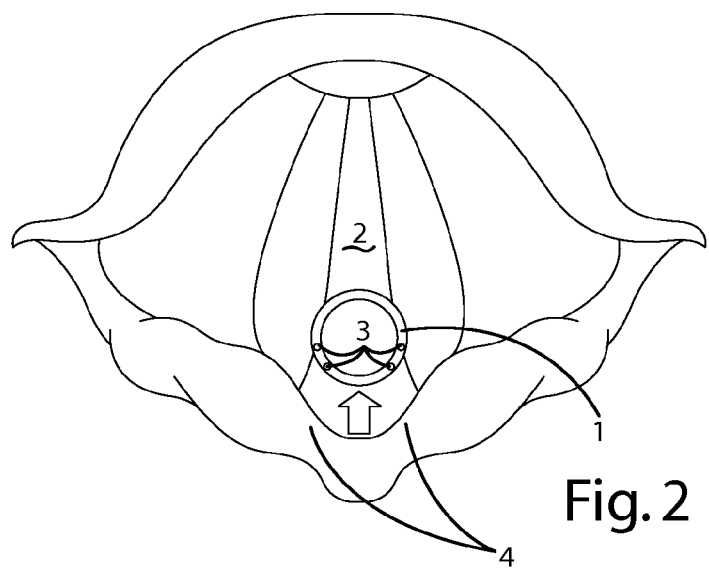
FIG. 2 is a top view of the prior art endotracheal tube including electrodes that are improperly positioned within the glottic opening, and out of contact with anterior target muscles.
Figure 3:
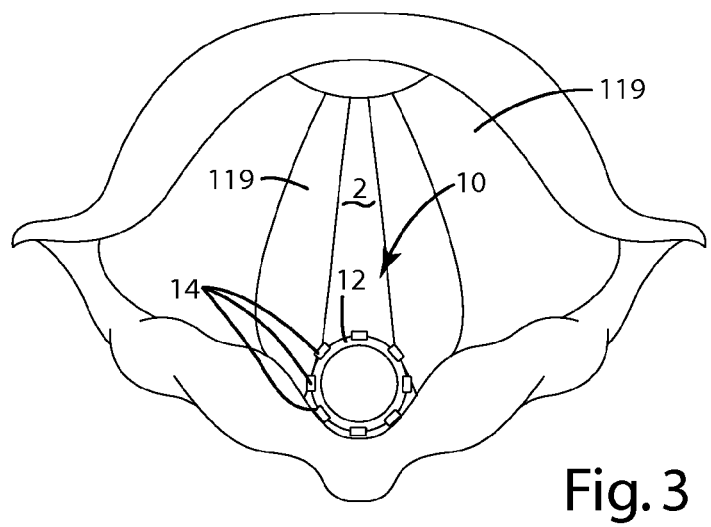
FIG. 3 is a top view of a current embodiment of a device in the form of an endotracheal tube including a multisensor array positioned within the laryngeal space.
Figure 4:
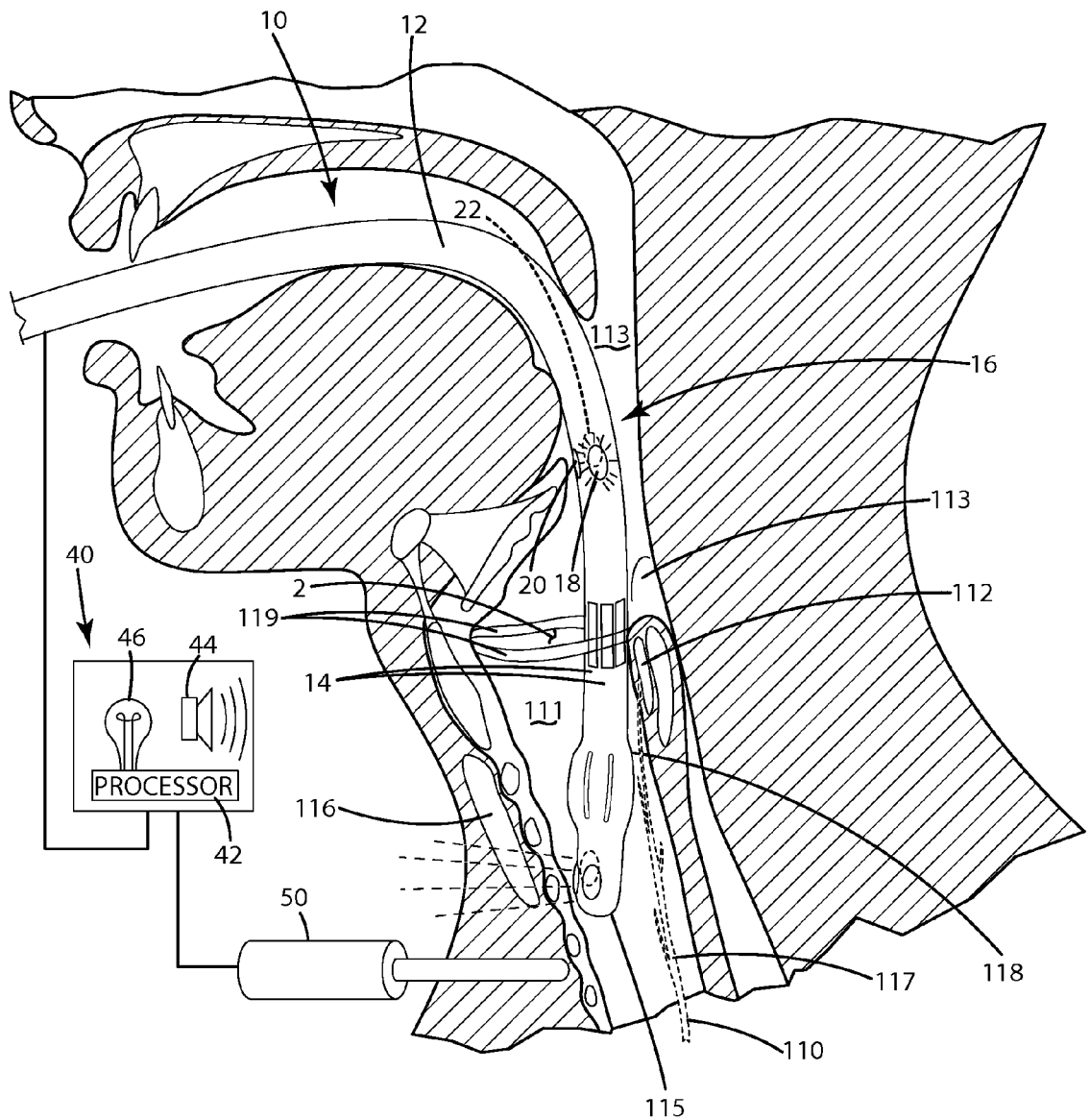
FIG. 4 is a side sectional view of the device of the current embodiment positioned within the laryngeal space.
Figure 5:
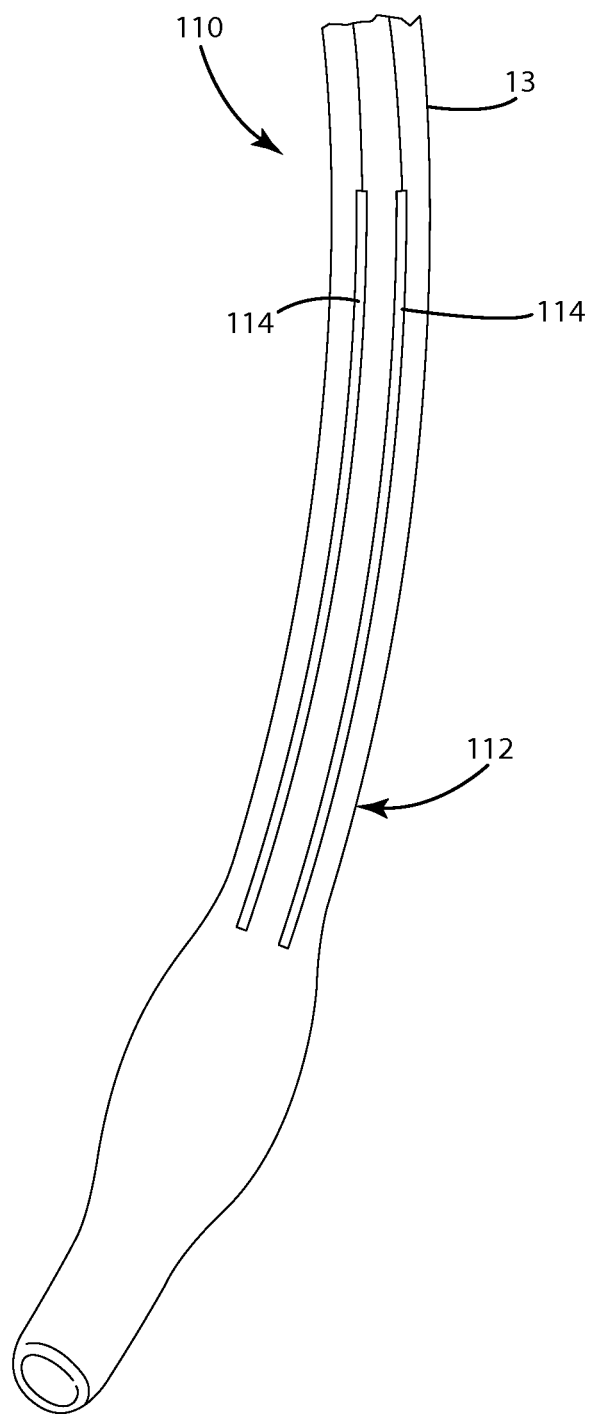
FIG. 5 is a side view of a first alternative embodiment of the device including one type of sensors.
Figure 6:
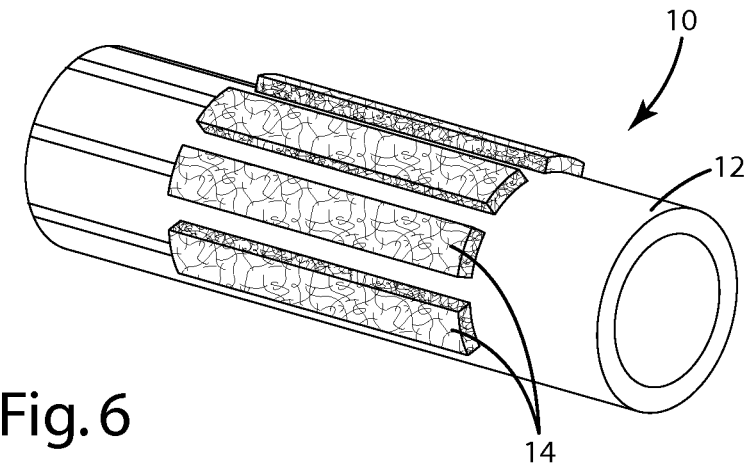
FIG. 6 is a perspective view of a portion of the current embodiment of the device illustrating one type of moveable electrodes.

A current embodiment of the device for monitoring nerves to detect nerve and/or muscle activity is illustrated in FIGS. 3-4 and 6 and generally designated 10. The device 10 can include a cannula 12, sensor 14 and an optional output element 40, as well as an optional electrical probe 50.

In general, the sensor 14 and probe 50 can be in communication with the output element 40. As shown in FIG. 4, a surgeon can engage the probe at a location where a target nerve, such as a recurrent laryngeal nerve 110, is suspected to be located. The probe 50 provides an electrical impulse, which in turn can be transmitted through the target nerve, to an associated target muscle, such as a laryngeal muscle, for example, posterior cricoarytenoid muscles 112 and/or the vocal cords 119. The subsequent activity of the target muscle can be measured or otherwise sensed by the sensors 14, and output to the output element 40 based on the measured response. The output element 40 can output information or an alert as to the location of the target nerve relative to the probe 50. In which case, the surgeon generally can perceive the location of the target nerve, and avoid further activity in the area so as to prevent unwanted damage or impairment to the target nerve.

While the embodiments herein are described in connection with a particular cannula, that is, an endotracheal tube used in the laryngeal space, it is to be understood that the device can be used in virtually any internal body space to monitor virtually any target nerve for purposes of avoiding unwanted damage or impairment to that nerve. For example, the device can be used in prostate, abdominal, pelvic or rectal surgery to prevent damage or impairment to associated nerves, e.g. pelvic nerves, pudendal nerves, etc. Alternatively, the device can be used to locate nerves that are to be rendered inoperative or to be used for acute or chronic neural stimulation.

As shown in FIGS. 3-4 and 5-8, the device of the current embodiment can include a cannula 12, which can be any device known to those of skill in the art as being insertable into a patient. For example, the cannula can be in the form of an endotracheal tube (ET tube) used in procedures conducted in or around the laryngeal space 111 or oropharynx 113, as shown and described herein, or in the form of other tubular or exploratory devices used for other procedures, such as prostate surgery, rectal surgery, colon surgery, or other surgical or investigative procedures.

Where implemented as an endotracheal tube, the cannula 12 can be used in anesthesia, intensive care, neonatal care and emergency medicine for airway management and mechanical ventilation. In use, the cannula, or ET tube 12 can be inserted through a patient's laryngeal space 111 and into the trachea 117 to ensure that the patient's airway is open by providing alignment and position of the tube relative to the glottis and the carina.

An exemplary procedure in which the device 10 may be used to monitor a nerve is thyroid surgery, as noted above. In such a procedure, the ET tube is inserted as shown in FIG. 4 through the glottic opening 2, with the sensors generally are positioned in the laryngeal space 111. The target nerves for monitoring in such a procedure is the recurrent laryngeal nerves (RLN), which are generally adjacent the thyroid glands 116. The target muscles, with which the RLN are associated, can be the left and right thyroarytenoid and right and left posterior cricoarytenoid muscles (PCAs). These muscles will exhibit activity when the RLN are stimulated, for example, by a probe 50 exerting an electrical stimulus adjacent or directly on the RLN. Due to variability in electrical responses from patient to patient, the optional targeting of multiple laryngeal muscles including these posterior and anterior muscles can in some cases improve the opportunity to detect small responses. For example, in addition to the PCAs, it is helpful to monitor the thyroarytenoid muscles within the vocal cords 119. The device 10 can be outfitted with multiple sensors that align with the vocal cords 119 in addition to the sensors that align with the PCAs when the cannula is properly positioned. Depending on the desired monitoring activity, a health care provider can select which target laryngeal muscles are contacted by the respective sensors, and subsequently, what muscle activity is output from the output element 40.

Optionally, a variety laryngeal nerves can be monitored with the device 10, depending on the procedure. For example, in addition to the RLNs, laryngeal nerves such as the non-recurrent nerves, superior nerves, inferior nerves and/or the vagus nerves may be monitored. Of course, where the device is used in other body spaces, other nerves may be monitored. Likewise, a variety of other muscles may be targeted for such monitoring, depending on the internal body space within which the device is used.

Returning to the general description of the ET tube, there are many types of such tubes. For example, ET tubes range in size from 3 mm to 10.5 mm in internal diameter. Different sizes of tubes are chosen based on the patient's body size with the smaller sizes being used for pediatric and neonatal patients. ET tubes having internal diameters larger than 6 mm usually include an inflatable cuff (which is not shown in FIG. 4 for simplicity). The ET tubes can also be constructed from a variety of materials, such as polymers.

The cannula 12 can be constructed from a biocompatible material that is either disposable or sterilizable. The cannula 12 can be formed of a plastic and can include a coating on the exterior surface 13 if desired. For example, the coating can be used to enable easier insertion of the cannula 12, or can include a material that limits or prevents an adverse reaction in the patient after insertion of the cannula 12.

The device 10 of the current embodiment can include sensors 14. As used herein, sensors can be anything that is able to detect nerve activity. Examples of suitable sensors include sensors having electrodes that detect electrical or pulse stimulation by an electrical probe, as well as chemical sensors. Suitable chemical sensors can be sensors that detect an increased presence of a chemical or specific compound that is associated with a change or modulation in nerve activity. For example, calcium or potassium sensors can be used.

As illustrated in FIGS. 3, 4 and 6, the sensors 14 can be in the form of a multi-sensor array that surrounds a portion, for example, a majority of an outer periphery of the cannula. In this array configuration, the larger number of sensors generally allow those sensors to conform to the anatomical geometry of the laryngeal space 111 so that at least one, two, or more of the sensors 14 are in monitoring proximity (defined below) to a target muscle, for example, a laryngeal muscle, such as the PCAs, thyroarytenoids, etc, and subsequently can measure activity of one or more of those muscles upon stimulation. Further, the array of sensors can be configured on a multiple channels. Thus, the array allows monitoring from different sensors (selected by a health care provider) and areas of the laryngeal space, around the cannula 12, and optionally, of different target laryngeal muscles (e.g., PCAs and/or vocal cords). This, in turn, can compensate for inadvertent cannula rotation within the laryngeal space as well as variations in muscle activity and monitoring in a variety of patients.

Optionally, the multi-sensor array 14 can include eight electrodes, with four on the left and four for the right sides of the cannula 12, in a generally symmetric orientation about the longitudinal axis of the cannula 12 as shown in FIG. 3. These electrodes can be connected to a nerve monitor with separate electrodes attached for ground and anode (stimulus return) on the sternum, for example. Further optionally, the electrodes in the array can be color coded, and can extend along the tube parallel to their laryngeal position until they branch off at the oral end of the cannula to help orient the health care provider to their deeper laryngeal position, as shown in the alternative construction of FIG. 5, which is described more below.

In general, a sensor, when in monitoring proximity to a target muscle or nerve, can measure activity of a muscle by simply detecting activity, or by detecting and measuring the level of activity against a predetermined value of activity. As used herein, monitoring proximity means that the sensor is close enough to the target muscle or nerve to detect that the muscle or nerve has been stimulated, or is undergoing some type of activity in response to a probe or other stimulation, e.g. mechanical manipulation. For example, monitoring proximity can mean that the sensor is close enough to the target muscle to detect electrical stimulation of the muscle. As another example, monitoring proximity can mean that a chemical sensor is close enough to the target muscle to detect a chemical change in the muscle indicative of stimulation or activity.

While shown in FIGS. 3, 4 and 6 as including a multi-sensor array positioned sensors around a majority of the cannula 12, the sensors can be combined in a single sheet sensor subdivided into separate detection zones. These zones can be calibrated so that the sensor 14 or output element 40 can determine which zones are detecting muscle activity or stimulation, and subsequently can communicate that information to the output element 40 to assist a health care provider in determining the rotational orientation of the ET tube 12 within the laryngeal space 111.

Figure 7:
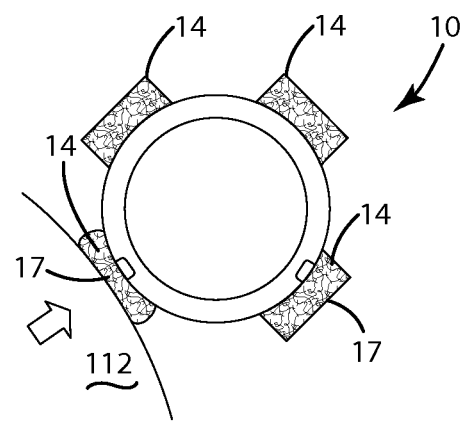
FIG. 7 is an end view of a portion of the current embodiment of the device illustrating the moveable electrodes of FIG. 6 conforming to anatomical geometry.
Figure 8:
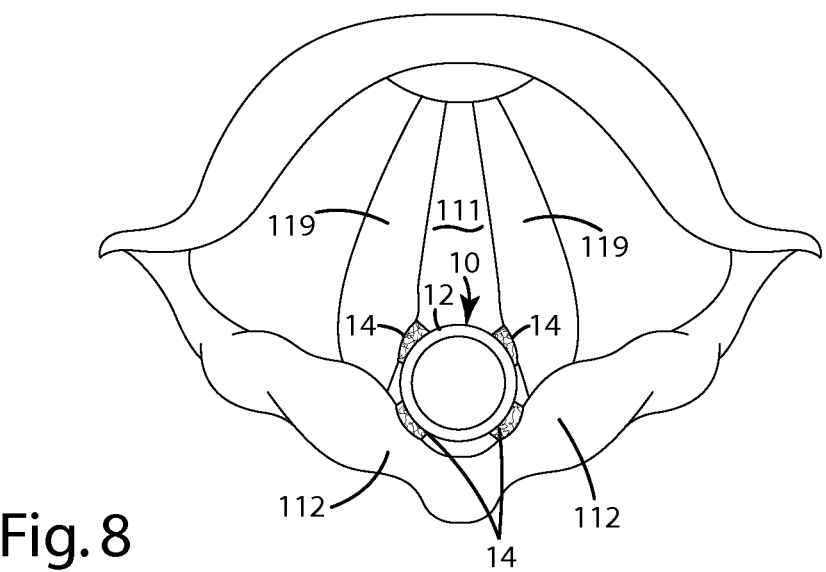
FIG. 8 is a top view of the device including the moveable electrodes of FIG. 6 conforming to the anatomical geometry of the laryngeal space.

Further, while the embodiments in FIGS. 3, 4 and 6 show eight sensors in an array that circumferentiate the cannula 12, fewer sensors can be used. For example, as shown in FIGS. 7 and 8, the device may only include one, two, three, four or other numbers of sensors, configured and spaced on and around the ET tube so that when the ET tube is properly spaced, each of those sensors contact respective target laryngeal muscles. As mentioned above, due to the array configuration that surrounds a portion of the cannula 12, different sensors can be adapted to align with different laryngeal muscles, for example, certain sensors can align with the vocal cords 119, while others can align with other target laryngeal muscles 112, for example PCAs.

In some cases, the array configuration can assist in enhancing and/or maximizing sensor contact with target muscles both anteriorily and posteriorily. This can be helpful across a variety of patients. For example, in some patients there appears to be a maximal muscle response from the vocalis muscles in the vocal cords, that is, the thyroartenoid muscles, 119 (anteriorly), whereas in other patients, the response appears maximal at the PCAs 112. Where multi-channel recording of activity detected by different sensors is optionally implemented, this can further enable the health care provider to choose electrode pairs or groups that are suitable for every patient, despite anatomic differences. Further, where the optional multi-sensor array is used, responses may be detected both anteriorly and posteriorly to assure that any response was detected, that is, to avoid a false negative error where a true muscle contraction is not detected.

Optionally, the sensors can also extend along the ET tube for a greater distance. For example, as shown in the first alternative embodiment of the device 110 in FIG. 5, the sensors can be in the form of electrodes 114 that extend along the tube for at least ⅓ or more of its length. The sensors are of a sufficient length that they are visible in the oropharynx or mouth to help orient the health care provider to the position of those electrodes in the laryngeal space. Further optionally, additional recording sensors can be placed on the tube in locations to engage convenient "non-relevant," that is, non-target, muscles to help distinguish artifact from true responses from target laryngeal muscles.

The sensors 14 used with the device 10 can vary in construction. As noted above, the sensors 14 can be in the form of exposed wire electrodes or plates that are in communication with the output element 40 and/or the probe 50. Generally, without some modification, these types of electrodes are fixed and immoveable relative to the cannula. As illustrated in FIGS. 6-11, however, the sensors of some embodiments herein can be reconfigurable from a first configuration to a second different configuration where the sensor conforms to the anatomical geometry of the space within which it is placed. As an example, a reconfigurable sensor can include moveable electrodes. As used herein, a moveable electrode means an electrode that includes at least one portion that moves relative to another portion or to the cannula or to the structure to which the electrode is attached, in order to allow the portion or the entire electrode to conform to the anatomical geometry of the space within which it is placed. As another example, a reconfigurable sensor can be configured so that it changes in shape, size or orientation relative to the cannula to which it is attached, and in so doing, conforms better to the anatomical geometry of the space within which it is placed. Optionally, the reconfigurable sensors, and in particular, the moveable electrodes, can be self-reconfiguring in that they are adapted to move, be moved, expand or otherwise reconfigure or alter in size to provide increased contact and/or maximized monitoring.

Referring to FIGS. 3 and 6-8, the reconfigurable sensor can be in the form of a moveable electrode having a plurality of fibers, strands or filaments 17 that are included in a pad like element, which resembles a felt or fibrous type structure. Any electrically conductive pad including fibers, strands or filaments suitable for sensing electrical activity in a target muscle is suitable for use with the device. Other materials that optionally may be used in the pad, or generally with the moveable electrode, include materials already used in surgery (e.g., brain cottonoids) soft, expandable materials such as Merocel® (commercially available from Medtronic Xomed, Inc.), or other materials used for epistaxis and sinus surgery. In some applications, the material used to construct the sensor can expand when wetted with moisture (either before insertion, or by the patient's secretions), enhancing contact with the target muscles while reducing trauma to the tissue. In addition, the pad can retain moisture to minimize impedance.

In operation, the sensor 14 can compress when engaged with an external force, so that its thickness decreases as shown in FIG. 7 upon engagement of the tissue 113. With this compression, the sensor generally reconfigures in shape yet maintains engagement with the tissue. FIG. 8 illustrates the device 10 with moveable sensors positioned in the laryngeal space, adjacent the target muscles 112 (e.g., PCAs), and the vocal cords 119, for monitoring the RLN. There, the sensors have been pushed against the target muscles 112, 119 and have generally reconfigured so as to provide suitable contact between them and the muscles 112 and 119. Because they compress, the sensors 14 also can reduce the forces exerted on the target muscles 112, 119 and other laryngeal tissue. This, in turn, can reduce trauma to those muscles when the device is used.

The sensors 14 shown in FIGS. 6-8 can be joined with the cannula 12 at a predetermined location that corresponds to the target muscle or nerve to be monitored upon insertion of the ET tube 12.

The sensors 14 can further include wires or other elements that are in communication with the output element 40. The sensors 14 can be joined directly to the exterior surface 13 of the cannula 12 via an adhesive, or can be embedded or molded within the cannula components, or can be joined to another structural element that is placed about the ET tube.

For example, the sensors 14 can be attached to an adjustable, removable sleeve (not shown) that can be used as a retrofit for currently available cannulas. For example, the sleeve can be manufactured separately and affixed to the cannula 12 before or after intubation. The latter allows a conventional ET tube of normal diameter to be positioned in the laryngeal space, followed by a sleeve slid over the ET tube. In this case, the ET tube can act as a stylet for the sleeve. Optionally, the sleeve can be adjusted up or down on the ET tube, and rotated about the ET tube.

The sleeve can include pockets (not shown) into which the sensors 14 are placed. Alternatively, the sleeve can include sensor holding strips that maintain the sensors 14 in place on the exterior surface of the sleeve. The sensors 14 can either be integrated within the material of the sleeve or can be added post production thereby enabling the sensors to both be removed and be changed depending on the type of sensor needed.

As noted above, the sensors 14 also can be attached directly to the exterior surface of the cannula 12. In such a configuration the sensor can be attached via surgical or other adherence technique that enables attachment of the sensor 14 without altering the functionality of the sensor 14. For example, if the sensor is a chemical or compound sensor, the adhesive can be selected so that it does not inhibit the function of the sensor.

As stated previously, the sensors 14 can be formed of a compressible material that enables the cannula 12 to be inserted into the patient without causing undue trauma to the patient's airway, laryngeal space, or other internal body space.

The device 10 of the current embodiment can also include an output element 40, which can be in communication, either via a direct electrical wire or wirelessly, with the sensor. In general, the output element can be an external EMG monitoring device that provides output indicative of measured activity of the target muscle and/or the target nerve when the probe 50 is positioned adjacent or on the target nerve. As shown in FIG. 4, the output element can include a controller or processor 42 that receives signals or data from the sensors 14, process as the signals, and outputs information or an alarm to a health care provider as to the sensed muscle activity, and thus the proximity of the probe 50 to the target nerve. The output of the element 40 can be an audible alarm from a speaker 44, and/or a visual alarm via a light 46 or screen, or by movement, such as vibration of the probe.

The device 10 of the current embodiment can also include an optional alignment element 16 including one or more alignment indicators 18, 20, 22 which provide output to a health care provider as to the location of the sensors 14, or other components of the device, within the internal body space. The alignment element 16 can be any device 16 capable of providing to the user an indication of the position of the sensors which can assist in appropriate sensor location. This in turn, can increase the accuracy of the nerve monitoring, and thereby limit the risk of unwanted nerve impairment and/or damage. The alignment element 16 can provide ongoing feedback to the user either as a receiver or a transmitter. The feedback can be in the form of a sound/alarm, a visual indicator, a vibration, electromagnetic energy or other form that provides position status of the sensor 14.

More generally, where the device 10 includes the optional positioning and alignment members, even where the device does not include sensors, it can assist in the precise alignment of the cannula in an internal anatomic space. As an example, this can help health care providers measure the depth of an endotracheal tube in a patient's airway, particularly in an operating room, an intensive care unit, hospital ward or an emergency room, where X-ray confirmation may be avoided.

The alignment element 16, and in particular, the alignment indicators 18, 20, 22 can be located in a variety of locations. Optionally, the alignment indicators 18, 20, 22 can be configured and oriented in a predetermined spatial relationship relative to features of the cannula 12 and/or the sensors 14. For example, the cannula 12 can include a cuff 118 and an insertion tip 115. The alignment element 16 can include a first set of alignment indicators joined with the insertion tip 115 of the cannula 12, and another set above the sensors 14 so that the alignment indicators are viewable in the oropharynx or mouth. The indicators 18, 20, 22 can illuminate or otherwise provide output through the tissue of the neck, or in the mouth, so that a health care provider can visually or otherwise perceive and assess the location of these indicators, and thus the different parts of the ET tube, in the laryngeal space. If the health care provider perceives that the alignment indicators are out of the appropriate location, for example, the ET tube tip indicators are not far enough in the trachea, or an alignment indicator is rotated relative to a preferred location, the health care provider can take corrective action and reorient the ET tube to an appropriate orientation and/or position within the laryngeal space.

As shown in FIG. 4, the alignment indicators can be in the form of light emitting diodes 18, 20, 22 or other electromagnetic transmitters. Optionally, the alignment element 16 can function by either transmitting to, or receiving from, external devices. Further optionally, insulated wires can connect the alignment indicators 18, 20, 22 to a power source (not shown) such as a disposable battery, a re-usable and/or rechargeable battery, a power source associated with the output element 40, or some other power source.

Again, in general, the alignment indicators 18, 20, 22 can provide readily understandable indications of whether the sensors 14 are properly aligned to provide accurate nerve monitoring. As an example, referring to FIG. 4, the indicators can be light emitting diodes 18, 20, 22 that are color coded to assist in determining ET tube position. The lights can be coded, for example with a red light 22 indicating a right side of the cannula, a blue light 18 indicating a left side of the cannula, and a yellow light 20 indicating a midline of the cannula 12. Generally, different emitted frequencies along the electromagnetic spectrum can differentiate between the individual transmitters, thus allowing accurate assessment of position or alignment in multiple planes. Alternatively, the alignment element 16 can implement transillumination, such as fiber optic illumination. With this type of illumination, fibers transmit light from an external source to illuminate the lateral and anterior borders of the cannula, thereby indicating the position of the sensors.

The embodiments herein and shown in the figures can enhance electrode-vocal cord contact, or generally can enhance sensor to target muscle contact, while optionally providing expedient feedback of position of the cannula within the respective body space. The different components of the embodiments may be used singly or in combination.

Use of the device 10 of the current embodiment will now be described in the context of monitoring an RLN in the laryngeal space. Of course the device can be used in the same or other internal body spaces with other muscles or tissue to monitor other nerves.

To begin, the cannula 12, complete with sensors 14, is inserted into the desired body space of the patient. In general, the sensor 14 can enable the health care provider to assess the location of the nerve to be monitored. While one purpose of monitoring the nerve can be to avoid damage or impairment of the nerve, another can be to detect the location of a nerve that is to be treated, and monitor the progress of a surgery or procedure designed to ablate, section, damage, reduce function or render useless the nerve. Another use would be to locate a nerve to allow stimulation, e.g. acute or chronic neural stimulation.

After insertion, and if included with the device, the optional alignment element 16 can be used by a health care provider used to ensure the sensors 14 are properly located adjacent the target muscle or nerve, and generally within monitoring proximity relative to the target muscle or nerve. For example, after insertion into the patient, transillumination of the alignment indicators 18, 20, 22 through the tissue of the subject near the sensor 14 (or other electromagnetic energy) allows assessment of ET tube 12 position transcutaneously, without the need for repeated endoscopy.

More specifically, immediately following intubation with a visual check of the ET tube 12 position, the alignment indicators 18, 20, 22 can be connected to the power source. Appropriate ET tube 12 position is determined by visualizing the transilluminated location of the LEDs 18,20,22 to assess correct depth and rotation of the ET tube 12. The optional alignment element 16 can be turned off, used intermittently or can remain powered to provide output to a health care provider regarding the location and rotational orientation to the ET tube 12, and to ensure it does not rotate or move during the surgery or procedure.

After insertion, the sensors 14 and an optional probe 50 can be connected to the output element 40, as well as a Stimulating Dissectors or other nerve stimulators. Further, the sensors 14 can be actuated to monitor nerve activity. When multichannel recording devices are available, additional sensors, or electrodes, optionally can be placed in monitoring proximity to non-relevant muscles to act as a control to rule out artifact and thereby reduce false positive nerve activity errors. In addition, impedances can be tested and a tap test performed on the larynx to further assess integrity of the set up. The initial stimulus intensity is typically set to 1 mA with alterations in the current based on clinical indications.

With the different elements appropriately connected, the health care provider can engage the probe 50 at a location where a target nerve, such as a recurrent laryngeal nerve 110 (FIG. 4), is suspected to be located. The probe 50 provides an electrical impulse, which in turn can be transmitted through the target nerve, to an associated target muscle, such as a laryngeal muscle, for example a posterior cricoarytenoid muscle 112 and/or a vocal cord 119 (FIGS. 4, 8). The subsequent activity of the target muscle can be measured or otherwise sensed by the sensor 12, and output to the output element. The output element 40, based on the measured response, can alert the health care provider as to the general proximity of the target nerve relative to the probe.

Optionally, where the multi-sensor array 14 (FIGS. 3-4, 5-8) is attached to an ET tube 12, that array can provide monitoring from different areas of the laryngeal space 111, thereby compensating for inadvertent ET tube rotation and allowing multiple recording modalities. The sensors can detect EMG responses from the laryngeal muscles arranged around the cannula, for example, the PCAs and the vocal cords. Further optionally, the multi-sensor array 14 can minimize the deleterious effects of the ET tube rotation by allowing the surgeon or technician flexibility in choosing the suitable recording montage for each patient. For example, the health care provider can choose to monitor all channels, and thus all target muscle electrical activity detected by all the sensors. Alternatively, the health care provider can monitor selected channels, corresponding to specific sensors in the multi-sensor array based on impedance testing and responses to electrical stimulation. Further alternatively, the health care provider can simply monitor in monopolar or bipolar modalities.

Figure 9:
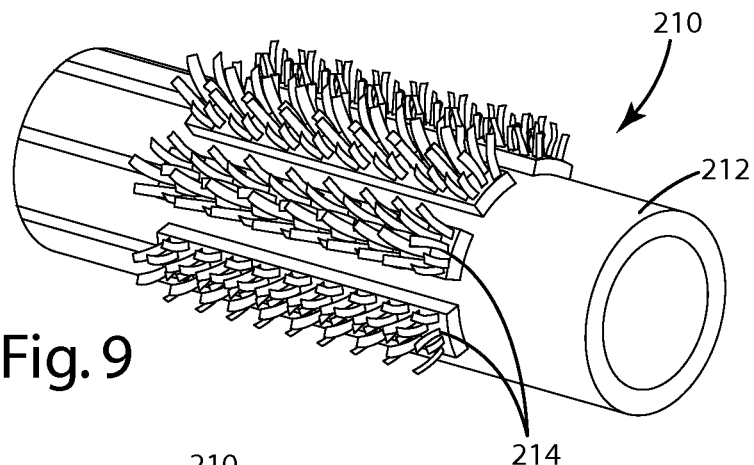
FIG. 9 is a perspective view of a second alternative embodiment of a portion of the device illustrating another type of moveable electrodes.
Figure 10:
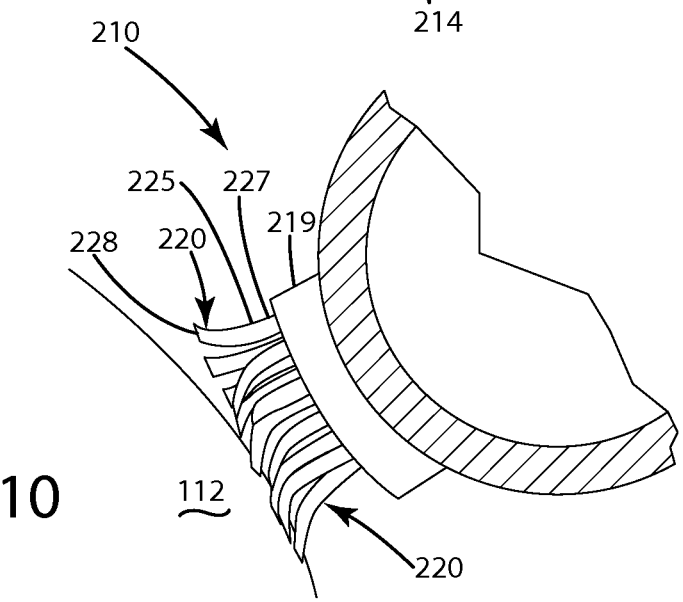
FIG. 10 is an end view of a portion of the second alternative embodiment of the device illustrating the moveable electrodes of FIG. 9 conforming to anatomical geometry.

Various other embodiments of the device 10 are contemplated. For example, a second alternative embodiment of the device is illustrated in FIGS. 8-11 and generally designated 210. Generally, FIGS. 9 and 10 illustrate portions of the device 210, and in particular, portions of the cannula 212 including sensors 214. This embodiment is similar to the above embodiment with a few exceptions. For example, the sensors 214 are in the form a reconfigurable sensor which includes moveable electrodes. More particularly, each individual moveable electrode 220 is attached with a base 219, which is joined with the cannula 212. The moveable electrode can be a flexible electrode, that is, it can bend or otherwise be reconfigured as shown in FIG. 10 when engaged by an anatomical feature, such as a laryngeal muscle 112. With this flexing, the electrodes can be brought within monitoring proximity of the target muscle or nerve in an atraumatic manner. Each of the individual electrodes 220 can include a distal end 228 and a proximal end 227, between which a medial portion 225 is disposed. The proximal end 227 can be joined with a base 219, which again can be joined with a cannula 212. Each electrode can be coated with a desired polymer and can include a metal or otherwise electrically conductive core. A variety of carbon structures also may be suitable for this particular flexible electrode.

Figure 11:
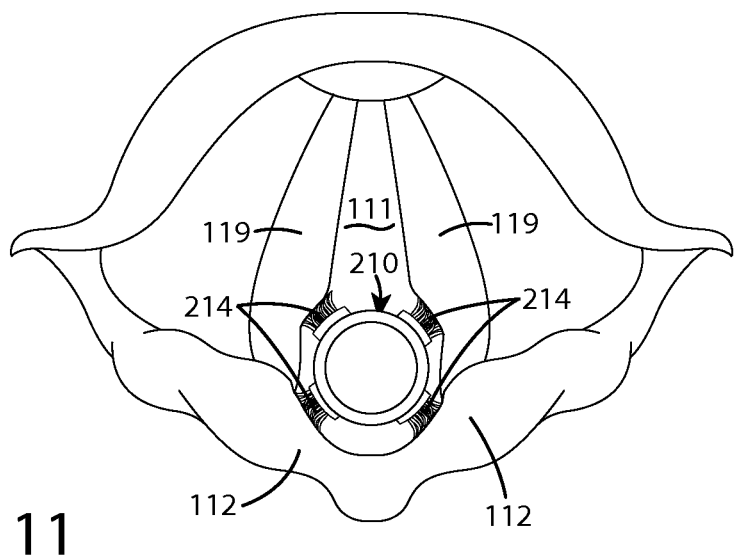
FIG. 11 is a top view of the second alternative embodiment of the device including the moveable electrodes of FIG. 9 conforming to the anatomical geometry of the laryngeal space.

FIG. 11 illustrates the device 210 of the second alternative embodiment with the cannula 210 inserted within the laryngeal space 111. The sensors 214 generally conform to the anatomical geometry of the laryngeal space 111, and in particular, the laryngeal target muscles 112. Upon making contact with the respective laryngeal muscles, the moveable electrodes 214 can reconfigure from a generally straightened mode to a flexed mode (as shown in FIG. 10), where the end of the flexible electrodes 220 move relative to the cannula 212. The flexible electrode thereby reconfigures in shape so as to fit within the laryngeal space yet still adequately contact the target laryngeal muscles 112.

Figure 12:
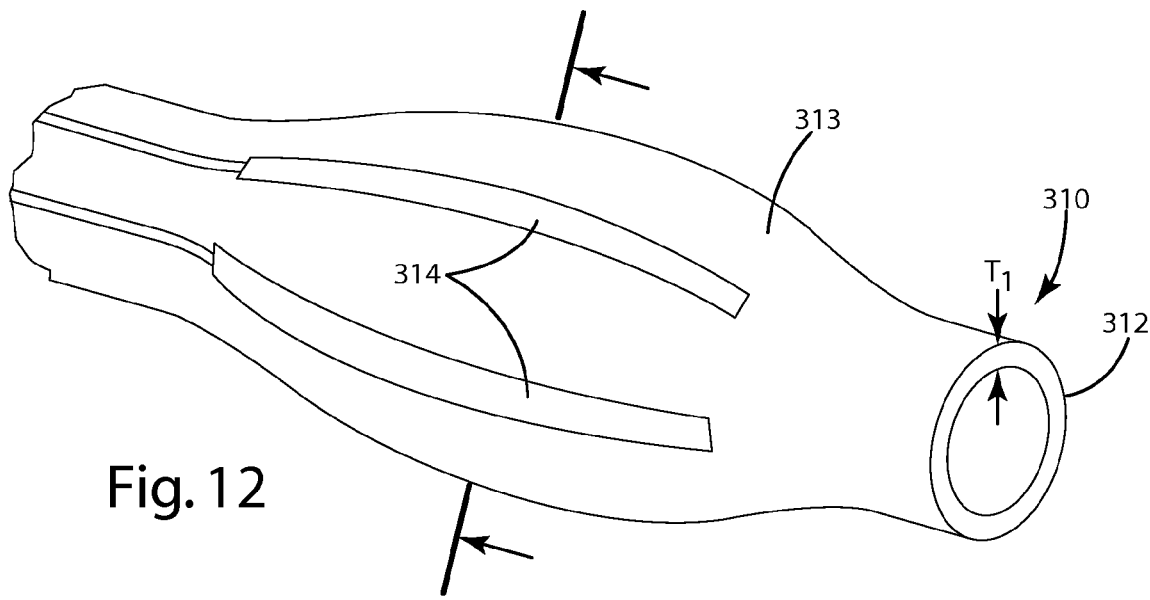
FIG. 12 is a perspective view of a third alternative embodiment of a portion of the device.
Figure 13:
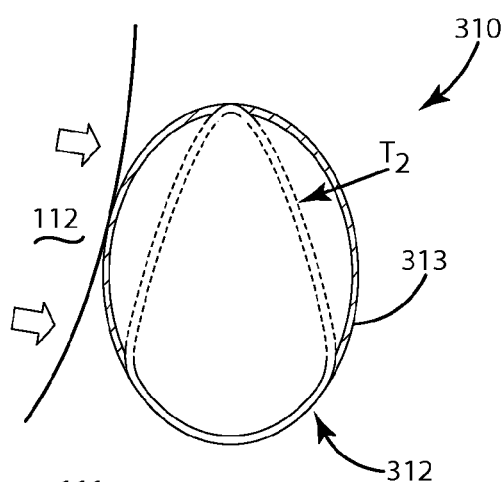
FIG. 13 is a section view of the third alternative embodiment of the device taken along lines 13-13 of FIG. 12, conforming to anatomical geometry.
Figure 14:
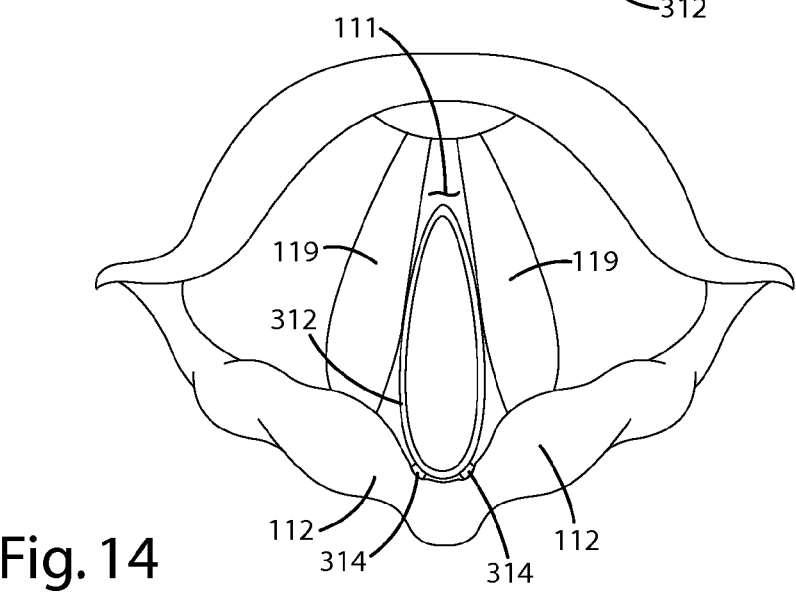
FIG. 14 is a top view of the third alternative embodiment of the device conforming to the anatomical geometry of the laryngeal space.

A third alternative embodiment of the device is illustrated in FIGS. 12-14 and generally designated 310. Generally, FIGS. 12 and 13 illustrate portions of the device 310, and in particular, portions of the cannula 312 including sensors 314. This embodiment is similar to the above embodiment with a few exceptions. For example, the cannula 312 can include a reconfigurable portion 313. Portion 313 is reconfigurable from a first configuration to a second configuration that conforms to the anatomical geometry of at least a portion of a body space, for example, the laryngeal space. As another example, the reconfigurable portion, or the cannula generally, can include a structure that enables it to reconfigure in size, shape or orientation, and in so doing conforms better to the anatomical geometry of the space in which it is placed.

As shown in FIG. 12, the electrodes 314 can be adapted to withstand some flexure due to the reconfiguration of the reconfigurable portion 313. The reconfigurable portion 313 of the cannula 312 can be constructed so as to change in at least one of size and shape so that it can fit through the glottic opening and/or generally conform to the laryngeal space and enhance contact between the sensors 314 and the target laryngeal muscle to measure activity of that muscle. As shown in FIGS. 13 and 14, the exterior surface of the reconfigurable portion 313 of the cannula 312 can change in shape when that portion is forced against an object, such as laryngeal muscle 112 and/or 119. Accordingly, the exterior surfaces of the endotracheal tube conform to the anatomical geometry of the same in an atraumatic manner.

To provide this reconfigurability, the reconfigurable portion 313 can include a wall that is of a thickness that is less than the remainder of the cannula. For example, the thickness $T_2$ shown in FIG. 13 of the reconfigurable portion 313 can be less than that of the thickness $T_1$ of the wall of the remainder of the cannula 312. As shown in FIG. 12, the difference in thickness can vary, for example, thickness $T_2$ can be ⅔, ¾, ⅓, ½, ¼ of the thickness $T_1$. Alternatively, or in combination, the reconfigurable portion 313 of the cannula can be constructed from a different material from the remainder of the cannula 312. As an example, the reconfigurable portion 313 can be constructed from an elastomeric or flexible material having a higher elasticity so that it readily changes in shape and/or forces, such as those exerted on the cannula 312 when inserted through the glottic opening. FIG. 14 illustrates the reconfigurable portion 313 which, due to its increased flexibility relative to the remainder of the cannula, changes in shape and conforms to the anatomical geometry of at least a portion of the glottic opening in an atraumatic manner. In this configuration, the sensors 314 also are brought into monitoring proximity to the target laryngeal muscles 112. With the configuration of the cannula in this embodiment, the contact between the target muscles and the sensors can be enhanced.

Figure 15:
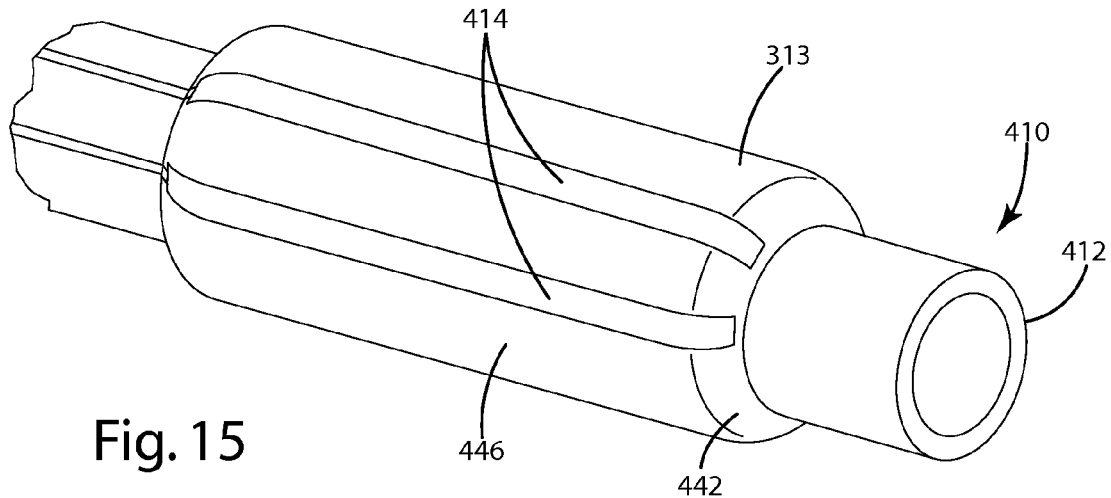
FIG. 15 is a perspective view of a fourth alternative embodiment of a portion of the cannula of the device including a support element.
Figure 16:
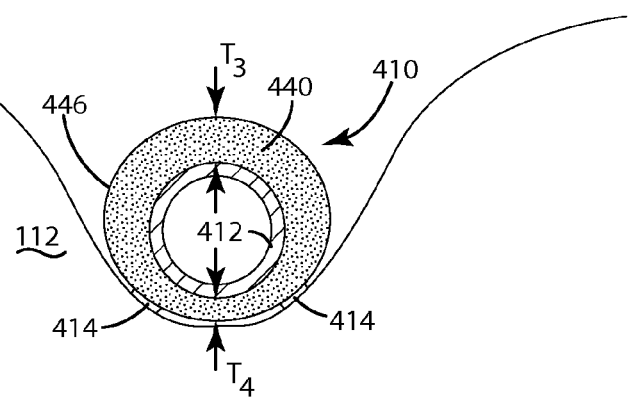
FIG. 16 is an end view of the fourth alternative embodiment of the device with the cannula including the support element conforming to anatomical geometry.
Figure 17:
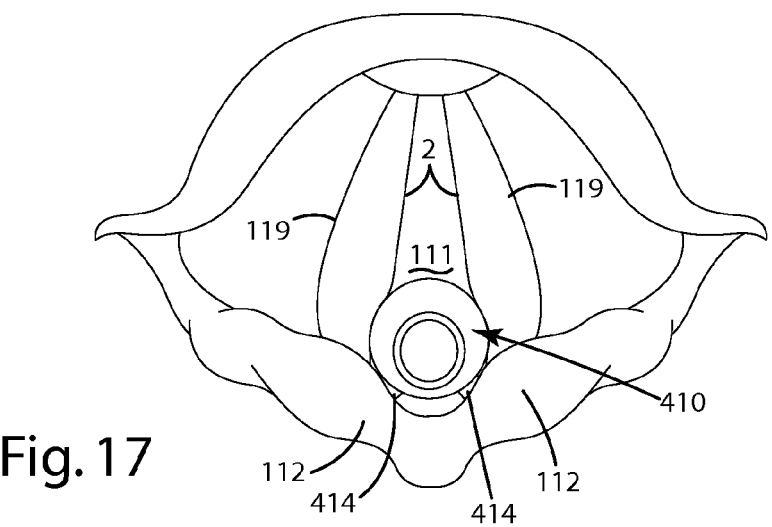
FIG. 17 is a top view of the fourth alternative embodiment of the device with the cannula including the support element conforming to the anatomical geometry of the laryngeal space.

A fourth alternative embodiment of the device is illustrated in FIGS. 15-17 and generally designated 410. Generally, FIGS. 15-16 illustrate portions of the device 410, and in particular, portions of the cannula 412 including sensors 414. This embodiment is similar to the above embodiments with a few exceptions. For example, the portion of the cannula 412 as illustrated includes a support element 440. This support element 440 is generally joined with the cannula 412 and generally surrounds the cannula 412. The support element 440 includes an outer surface 446 that is adapted to engage the anatomical geometry of the laryngeal space or other body space in which the cannula is positioned. As can be seen, the support element is generally of a size and dimension that is greater than that of the cannula 412. The dimensions of the outer diameter, can be selected based on the amount of space within which the device is to be positioned.

The support element can be integral with the endotracheal tube or a completely separate element that is positioned over the endotracheal tube or cannula 412. Further optionally, the support element can simply be an integral part of the endotracheal tube or cannula. Regardless of the alternative constructions in the embodiments described herein, the endotracheal tube is considered to "include" the support element where the support element is part of the device.

The device 410 can include sensors 414 joined with the support element 440. The sensors 414 can be embedded within the support element 440 or simply attached to an outer surface. The support element can enable movement of the sensors 414 relative to the cannula 412 so that the sensors are within monitoring proximity to a target laryngeal muscle. Accordingly, the activity of the related target nerve can be measured when the nerve is stimulated by an electrical probe such as that described above.

As shown in FIG. 16, the support element 440 can be compressible so that it can reconfigure from a thickness $T_3$ to $T_4$ when forced against an object, such as a laryngeal muscle 112. In so doing, with the reduction of thickness, the support element compresses in the area where the force is applied. Generally, with the compressibility of the support element 440, the contact between the sensors 414 and the target laryngeal muscles 112 can be improved.

The support element 440 can be constructed from a variety of materials. As an example, those materials may include compressible materials, such as elastomeric materials, foam materials, closed cell foam materials, an air filled bladder, or combinations of the foregoing.

Figure 18:
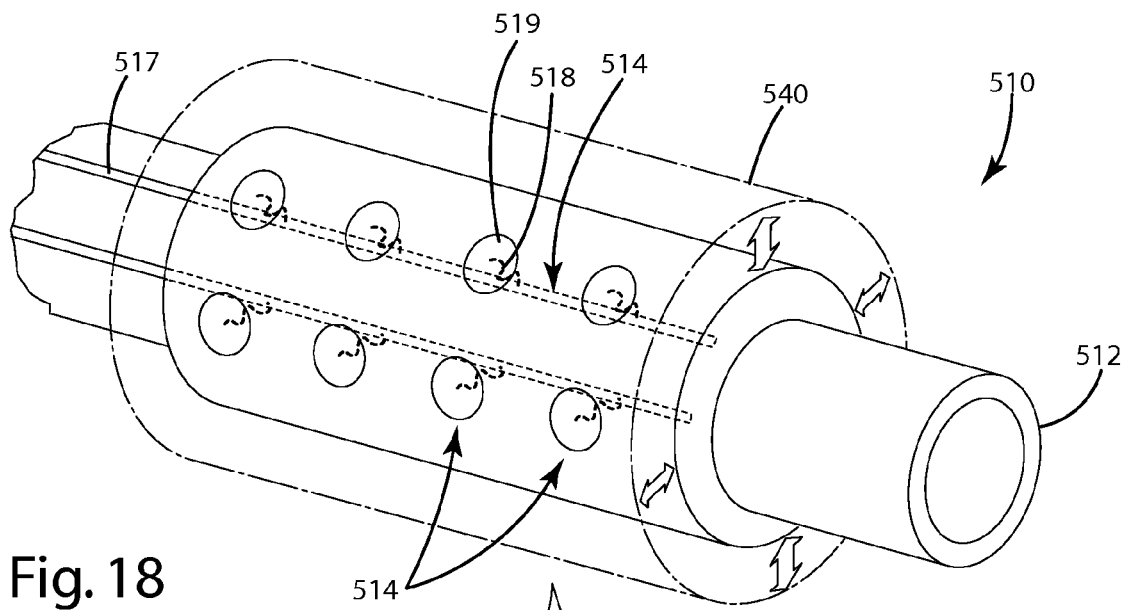
FIG. 18 is a perspective view of a fifth alternative embodiment of a portion of the cannula of the device including a support element.
Figure 19:
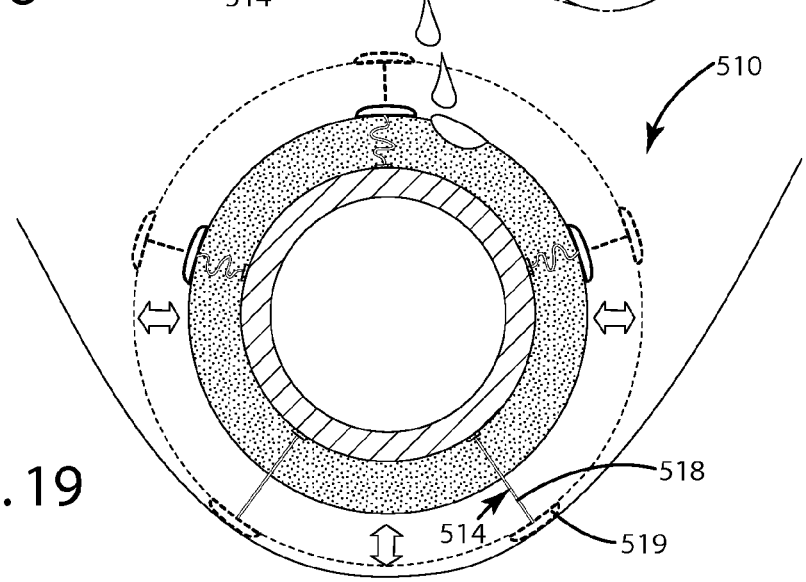
FIG. 19 is an end view of the fifth alternative embodiment of the device with the cannula including the support element illustrating expansion and compression of the support element.
Figure 20:
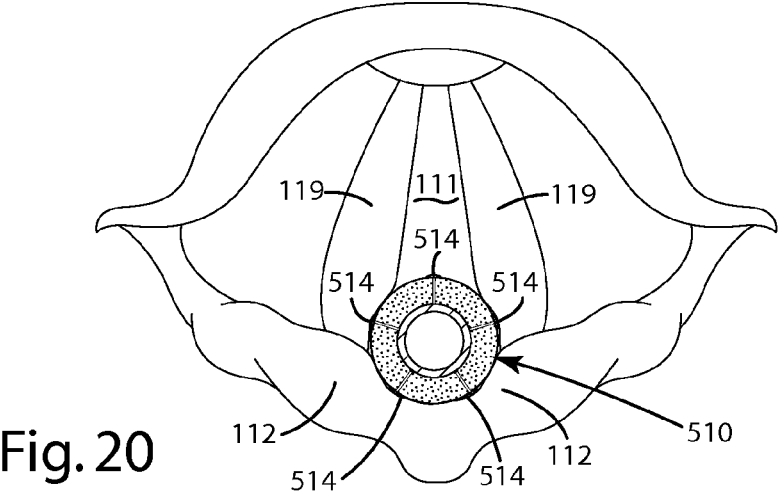
FIG. 20 is a top view of the fifth alternative embodiment of the cannula including the support element conforming to the anatomical geometry of the laryngeal space.

A fifth alternative embodiment of the device is illustrated in FIGS. 18-20 and generally designated 510. Generally, FIGS. 18-19 illustrate portions of the device 510, and in particular, portions of the cannula 512 including sensors 514. As shown in FIG. 18, the cannula 512 includes another support element 540, which may either be integral with the cannula 512 or separately joined with the cannula. This support element can be adapted to expand or contract, depending on different environmental conditions. As one example, the support element 540 can be constructed from a sponge-like material, which when dry is in a compressed mode. When wetted, the sponge material can expand outward as shown in FIGS. 18-19 in broken lines to achieve a greater size and dimension. This greater size and dimension can enhance the contact between the sensors 514 and the target muscles for monitoring of nerves associated with those muscles. Alternatively, the support element 540 can be constructed so that it compresses from an expanded mode to a compressed mode when subjected to liquids. Within this construction, as the support element 540 and cannula 512 enter a body space, secretions of the body space can cause the support element to reduce in size and generally conform to the anatomical geometry of the body space.

In general, when the support element 540 expands, it increases in size and/or dimension within the general body space, for example, the laryngeal space. This in turn can enable the cannula/endotracheal tube to conform to the anatomical geometry of the body space in an atraumatic manner. Similarly where the support element is a compressible element, it can decrease in size when forced toward a target laryngeal muscle. In turn, the endotracheal tube within which the compressible element is included can conform to the anatomical geometry of the body space in an atraumatic manner.

As shown in FIGS. 18 and 19, the sensors 514 can be of a particular construction to accommodate the expansion and/or compression of the support element 540, and the relative movement of the outer surface of the support element relative to the cannula 512. For example, the electrodes can include a primary wire 517 that couples to multiple secondary wires 518. These secondary wires 518 can be in a furled or coiled or otherwise accordion-like configuration when the support element is in a compressed mode. Generally, the wires can be considered to be unextended in this configuration. When the support element transitions from a compressed mode to an expanded mode, for example, when it is wetted, the secondary wires 518 unfurl or uncoil as shown in FIG. 19.

The secondary wire can include a portion that is adjacent the outer surface of the support element 540. This portion can provide the desired monitoring of the target muscle. Alternatively, the ends of the secondary wire 518 can be joined with caps 519 that are positioned on the outer surface of the support element. These caps can provide increased surface area for engagement of the sensor 514 with the target nerve, and generally can enhance the engagement of the sensor with a target muscle to ensure that the activity of the nerve is measured when stimulated.

Optionally, the sensors, and in particular, sensors including coiled or furled wires 518 and caps 519 of this embodiment can be substituted for the sensors of other embodiments. As an example, these sensors can be used and joined with the strips of the embodiments shown in FIGS. 21-30, or other permutations of those or other embodiments, and can operate in a similar manner.

A sixth alternative embodiment of the device is illustrated in FIGS. 21-24 and generally designated 610. This embodiment is similar to the above embodiments with a few exceptions. The device 610 can include a support element 640 that is joined with the cannula a predetermined location generally corresponding to the laryngeal muscles 119 or other muscles depending on the internal body space in which the cannula (here, shown as an endotracheal tube 612) is to be disposed. The support element 640 can include a sensor 614 on its exterior. The sensor 614 can include generally identical physical components as the support element 640, however, the sensor can also include the other features of the sensors described in other embodiments herein.

The support element 640 and sensor 614 can be a layered construction, where the sensor is located on the exterior of the support element 640 so that it can satisfactorily measure the activity of a target laryngeal muscle when the sensor is placed in monitoring proximity to that muscle.

Figures 21, 22:
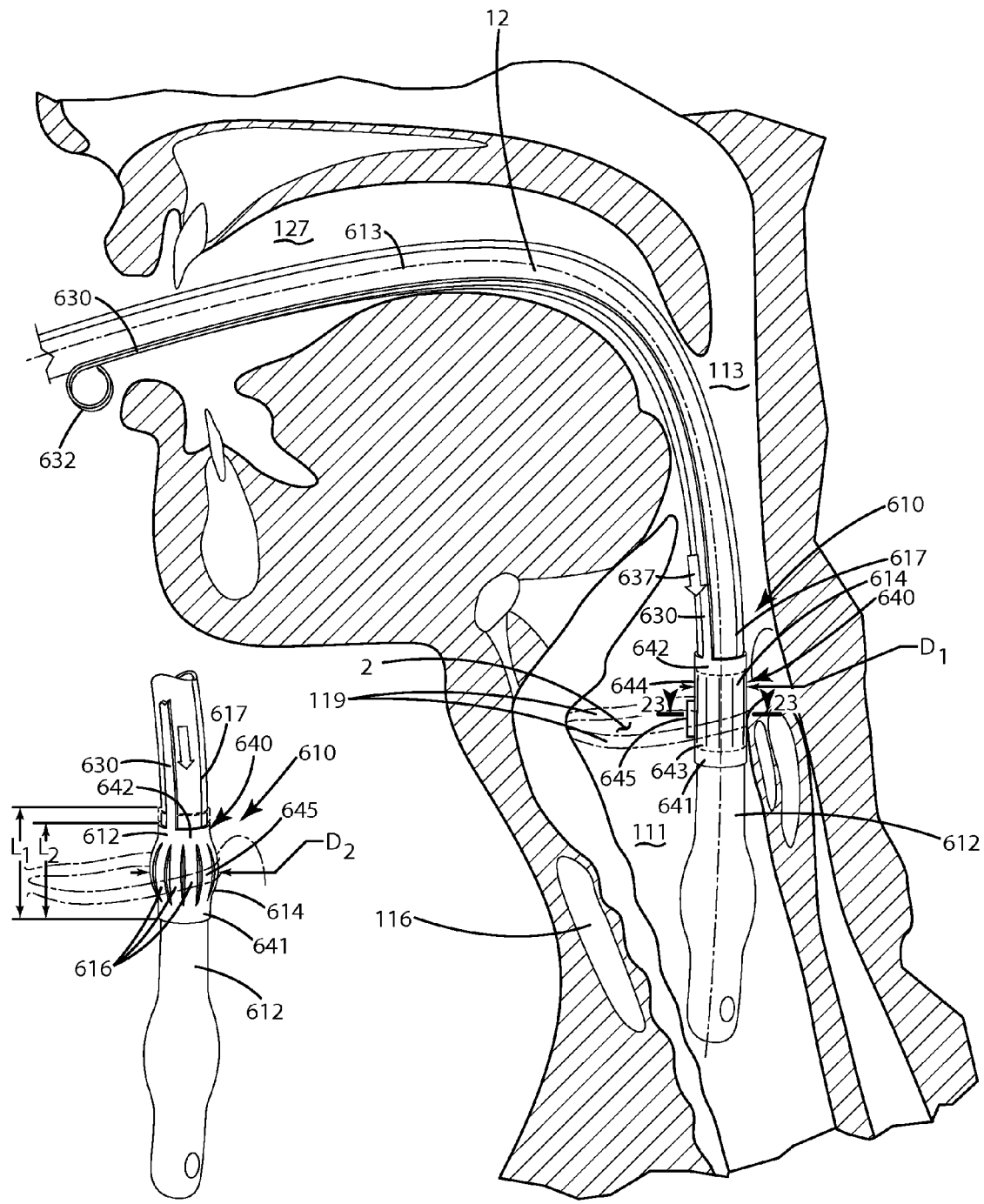
FIG. 21 is a perspective view of a sixth alternative embodiment of the device including another support element in a retracted mode or first configuration.
FIG. 22 is a perspective view of the sixth alternative embodiment of the device with the support element in an expanded mode or a second configuration.
Figure 23:
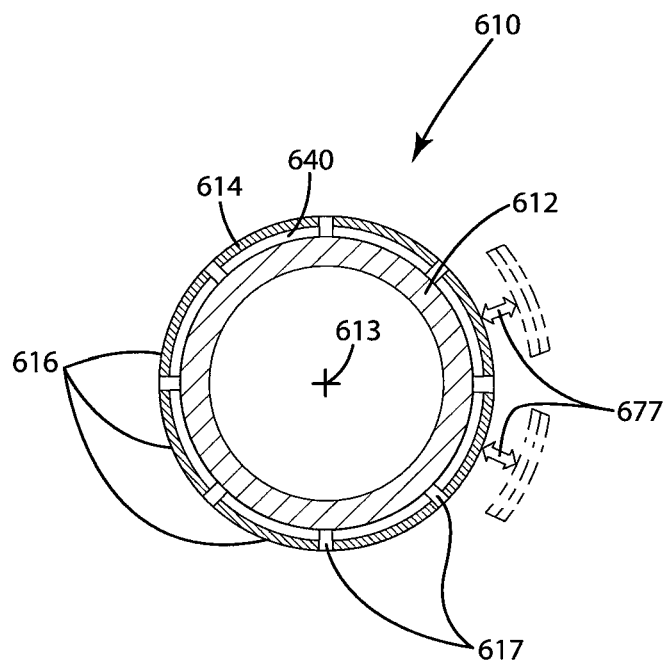
FIG. 23 is a section view of the sixth alternative embodiment of the device taken along lines 23-23 of FIG. 21.

As shown in FIGS. 21-23, the support element 640 can include one or more individual strips 616 that extend generally parallel to a longitudinal axis 613 of the cannula. The strips can be located relative to the cannula 612 so that when the cannula 612 is placed in an internal body space, such as a glottic opening 2, the strips, and any related sensor components, align with a target muscle and/or target nerve for monitoring, for example, a target laryngeal muscle 119.

Optionally, as with all of the designs of all of the embodiments herein, any of the sensors, support elements, and/or other structures can be completely integrated into and form a part of the respective cannula, whether an endotracheal tube or not, or alternatively can simply be attached to or otherwise joined with any generic tube that is to be used for a procedure in some internal anatomic space.

The strips 616 can be of an elongated configuration, and although shown as rectangular strips, the strips can be of a variety of geometric shapes. For example, the strips can be wavy along their peripheries, or they can include interlocking features.

The strips 616 also can be separated by gaps 617 as better shown in FIG. 23. These gaps can be selected and sized depending on the desired spacing of the strips relative to one another. Of course, where it is desired that the strips be placed immediately adjacent one another, the gaps can be miniscule.

Each of the individual strips 616 can include a first end 643 and a second end 644 with a central portion 645 disposed therebetween. The respective strip ends can be joined with connection elements 641 and 642. Although shown as including two connection elements, one of the connection elements can be eliminated from the device 610, or additional connection elements can be added, as desired. Generally, at least one of the connection elements 641 or 642 is joined with the multiple strips 616 to secure them to the cannula 612.

The connection elements 641 and 642 can be configured so that they circumferentiate in whole or in part at least a portion of the cannula 612 to hold the strips adjacent the cannula, at least at the ends of the strips. The connection elements 641, 642 can be in a ring or tubular configuration and can be of a slightly larger dimension than the exterior circumference of the cannula 612. If desired, the internal circumference of one of the connection elements can be the same size or slightly smaller than the exterior circumference of the cannula 612 so as to provide a snug fit around the cannula and hold at least a portion of the support element 640 in a fixed orientation relative to the cannula 612, and more particularly relative to the longitudinal axis 613 of the cannula 612. The other connection element can have a larger internal diameter so that it can move relative to the cannula 612.

Returning to FIGS. 21 and 22, the sensor 614 and more particularly the portion of the sensor associated with the support element can be in the form of electrodes, and can be connected via wires 617 to an output element as described in the embodiments above, and can likewise operate like the sensors described in the embodiments above.

Alternatively, the sensor 614 can be in wireless communication with an output element, such as those described in the embodiments above. The output element can provide output indicative of measured activity of the at least one of a nerve and the muscle when a probe (described above) is positioned adjacent or on the target nerve.

Figure 24:
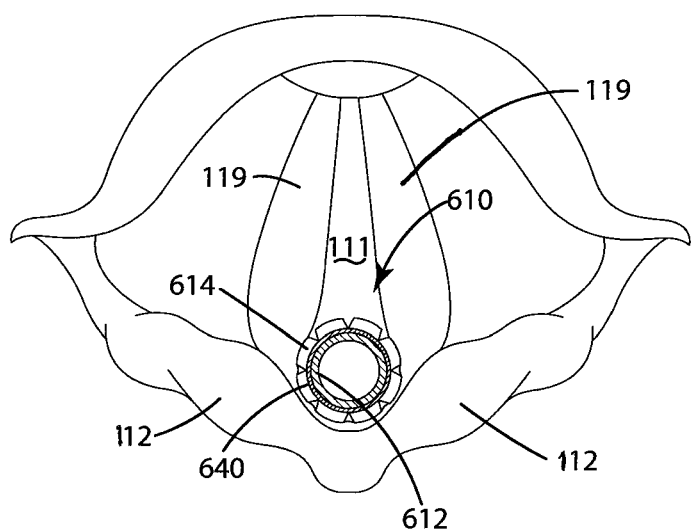
FIG. 24 is a top view of the sixth alternative embodiment of the device including the support element with the device conforming to the anatomical geometry of the laryngeal space.

Optionally, where the sensor 614 includes multiple strips, those strips or portions of them can include multiple electrodes that are configured in an array, and that circumferentiate an outer surface of the endotracheal tube or cannula 612. As shown in FIG. 24, when inserted in the laryngeal or other internal body space as described in connection with the embodiments above, this array can be configured so that at least two of the electrodes, that is at least two of the sensors on the strips, can be in electrical contact with at least one of the target muscles and/or nerves, regardless of the orientation of the endotracheal tube within the internal body space when the device is in an expanded mode.

Further optionally, as with the other embodiments herein, where the sensors, or portions of them, include multiple electrode arrays, a health care provider can readily compensate for suboptimal rotational positioning of the sensors, cannula and/or device in general by testing and then selecting the electrode(s) with the best signal response for the particular patient and the particular device position.

Even further optionally, the strips can operate so that when expanded, they automatically engage and geometrically conform to the anatomic space within which they are positioned. When expanding, the strips can also move and reorient the device, for example, the cannula and/or the sensors can be moved by the strips expanding and engaging the anatomic space, which in turn can generally center these components within the anatomic space and/or bring the sensors into better engagement with the respective target muscles and/or tissue.

Returning to FIG. 21, the first connection element 642 can include or can otherwise be enjoined with an actuator 630. The actuator 630 can extend along a portion of the cannula 612 to a location where at least a portion of the actuator is manually graspable by a healthcare provider, such as a surgeon. As illustrated in FIG. 21, the actuator 630 can be in the form of a thin, elongated member that extends along the cannula 612 from the connecting member 642 to a handle 632. Although this handle is generally ring shaped, it can be of a variety of other shapes, for example, it can be in the shape of a J, it can include multiple finger holes, or it can be in the form of a sleeve that wraps around the endotracheal tube 612. Optionally, the handle 632 is located above the oropharynx 113. For example, it can be located somewhere inside, or even outside (as shown) the oral cavity 127 when the endotracheal tube 612 is fully inserted in a desired location in the trachea 111, with the support element 640 and related sensors 614 in registration with the target laryngeal muscles 119.

In FIG. 21, the device, and more particularly, the support element is shown in a retracted mode having a dimension D1, which corresponds to a first dimension. When the actuator 630 actuates the support element 640, the support element is reconfigured from the retracted mode shown in FIG. 21 to the extended mode shown in FIG. 22, where the device, and more particularly the support element has a larger dimension D2. The actuator 630 moves in the direction 637 as shown in FIG. 21, thereby moving the first connection element 642 toward the second connection element 641. In turn, this causes the strips 616 to move outwardly from the cannula 612 some preselected distance 677 as shown in phantom in FIG. 23. This distance 677 optionally can be 0.1 cm to about 4 cm, further optionally about 0.5 cm to about 2 cm, or other distances depending on the application. The strips 616 can bow or bend outward in this movement. For example, strips can move radially outwardly from the longitudinal axis 613 of the cannula 612, and in so doing, can also slightly bend, bow or arch outward.

Optionally, the support element and/or sensor is constructed from a flexible material, such as a polymer or other flexible material. The strips 614 can form a generally convex outer dimension D2 (FIG. 22) which, as mentioned above, is larger than the dimension D1 (FIG. 21). Further optionally, the first connection element 642 is generally moveable toward the second connection element 641 as shown in FIG. 22. With this movement of the first connection element, the length of the support element can change in transitioning from the retracted mode to the extended mode. For example, the length can change from a greater length L1 to a lesser length L2 as illustrated in FIG. 22. The difference between lengths L1 and L2 optionally can be about 0.1 cm to about 8 cm. Further, optionally, about 0.5 cm to about 2 cm, or other lengths as desired.

Referring to FIGS. 21-23, the central portion 645 of each of the plurality of strips 616 generally moves a larger distance away from the cannula 612 than the first 643 and second 644 ends of the strips 616 when transitioning to the extended mode. In turn, the central portion extends or projects outwardly from the cannula more than other parts of the strips in the extended mode. This can be a result of the generally outwardly bowing, bending or arching of the strips. Optionally, this also can result in the support element and/or sensors operating somewhat like the expanding mechanism in a Chinese lantern, so that the device transforms to a Chinese lantern-like configuration in the expanded mode. Of course, the strips can be modified so that other parts extend outwardly more than the central portion if desired.

FIG. 24 illustrates the engagement of the device 610, and in particular, the sensors 614 with their respective target muscles 112 and/or 119 within the laryngeal space 111. As shown there, the movement of the sensors and/or support elements enables the device to generally self-position or self-mobilize itself automatically when operated, as with the other embodiments described herein. For example, when the device converts from the retracted mode to the expanded mode, the strips 616 and sensors 614 move outwardly, and in so doing engage the surrounding tissue and/or muscles. This inherently can cause the device to self-position itself, and optionally center itself, within the anatomic space (as shown there, in the larynx) in an atraumatic manner. It also can cause the sensors to be placed in the appropriate position so that they precisely engage and/or are brought into monitoring proximity to target muscles 112 and/or 119. More generally, positioning the device well, by auto-conforming to the surrounding anatomic space, can provide more precise, effective and atraumatic means to contact, stimulate, record, measure, affect and/or ablate the target tissue. The other functions of the device 610 and signal output is similar to that of any of the embodiments described herein, and therefore will not be described again here.

Figure 25:
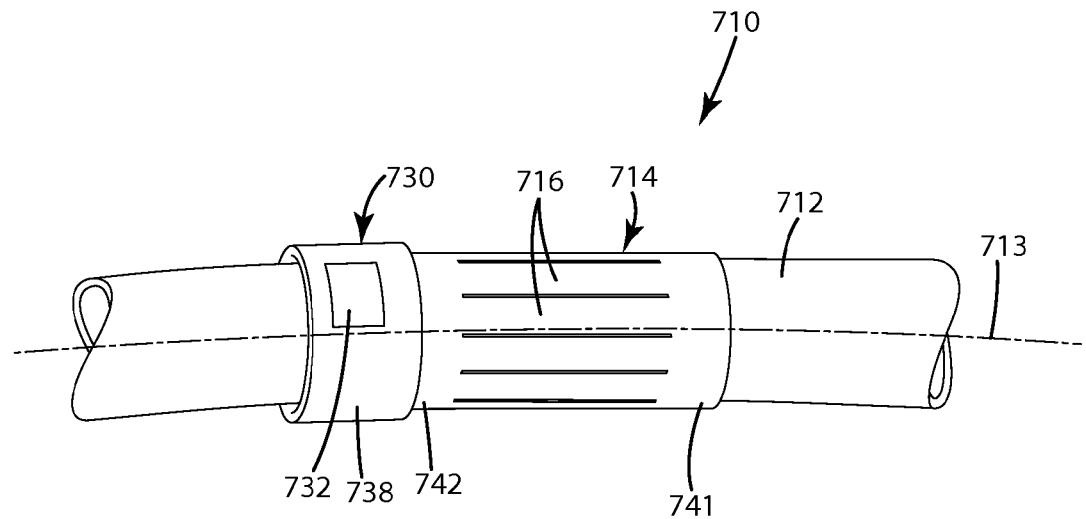
FIG. 25 is a perspective view of a seventh alternative embodiment of the device, including an expandable sensor and a remote actuator, with the device in a retracted mode or a first configuration.
Figure 26:
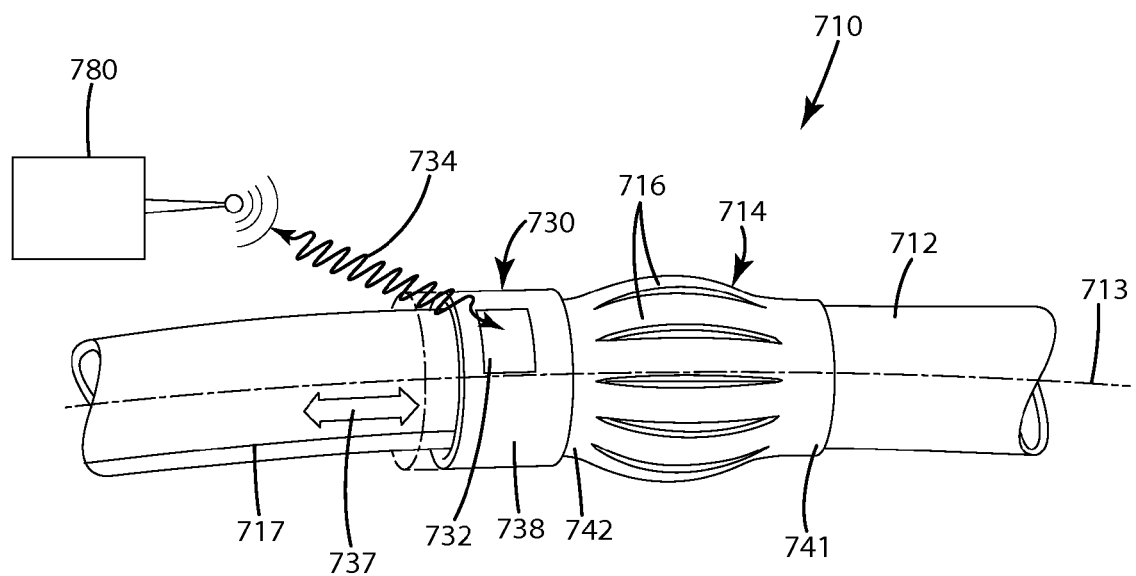
FIG. 26 is a perspective view of the seventh alternative embodiment of the device, including an expandable sensor and the remote actuator, with the device in an extended mode or a second configuration.

A seventh alternative embodiment of the device is illustrated in FIGS. 25 and 26 and generally designated 710. This embodiment is similar to the embodiments described above with one difference being that the support element is absent. As shown in FIGS. 25 and 26, the sensor 714 of the device 710 includes the multiple strips 716 and connection elements 741 and 742. There is no underlying support element in this embodiment. Another difference is that the actuator 730 can be an automated or non-manual actuator. For example, the actuator 730 can be placed adjacent the sensor 714 (or support element if included) and can operate like a solenoid, so that the housing 738 of the actuator 730 moves relative to cannula 712. The cannula 712 may include a magnetic or other solenoid element therein or attached thereto to enable the housing 738 to move when actuated. The housing can be adapted to engage the sensor 714, for example one or more of the connection elements 742 and/or 741. When the housing 738 engages the connection elements, for example as shown in FIG. 26, that connection element 742 moves toward the other connection element 741. In so doing, the multiple strips 716 are converted from the retracted mode as shown in FIG. 25 to the extended mode as shown in FIG. 26. In turn, the strips 716 can expand, moving outward from the cannula 712, and can engage the corresponding target muscle and/or target nerve as with the embodiments above. Optionally, the sensor 614 can be in electrical communication with an output element (not shown), like those described in other embodiments herein, via a wire 717, and accordingly can monitor the target muscle and/or nerve.

The actuator 730 can include one or more magnets or other suitable components (not shown) to move the housing 738. This component can be in communication with internal circuitry (not shown) of the sensor and/or a transmitter/receiver 732. The transmitter/receiver can send and/or signal 734 from an external or remote transmitter/receiver 780.

The transmitter/receiver 780 can be operated by a healthcare provider at a desired time to expand or retract the sensors (and/or support elements if used with the sensors) and acquire a desired engagement with the target laryngeal muscle or target nerve, or other muscle or nerve. In particular, the transmitter/receiver 780 can enable a healthcare provider to operate the actuator 730, thereby moving the housing 738 in the directions of the arrow 737. In turn, this extends or retracts the multiple strips 716 to configure the sensor 714 in a desired orientation relative to a target muscle and/or nerve.

Optionally the second connection element 741 of the sensor 714 can be fixed relative to the cannula 712, while the first connection element 742 can move and/or slide along the cannula. Such a configuration enables the housing 738 to engage the first connection element 742 and move it relative to the cannula 712. Due to the second connection element 741 being fixedly joined with the cannula 712, or generally immovable, the forces exerted by the housing 738 are translated to the strips 716, which in turn bend, arch or bow outwardly, radially away from the cannula 712, and specifically its longitudinal axis 713. Further optionally, although described as solenoid-operated, the actuator 730 can include other motors, drives or mechanisms that engage the sensor 714 to convert it between the retracted and extended modes.

Figure 27:
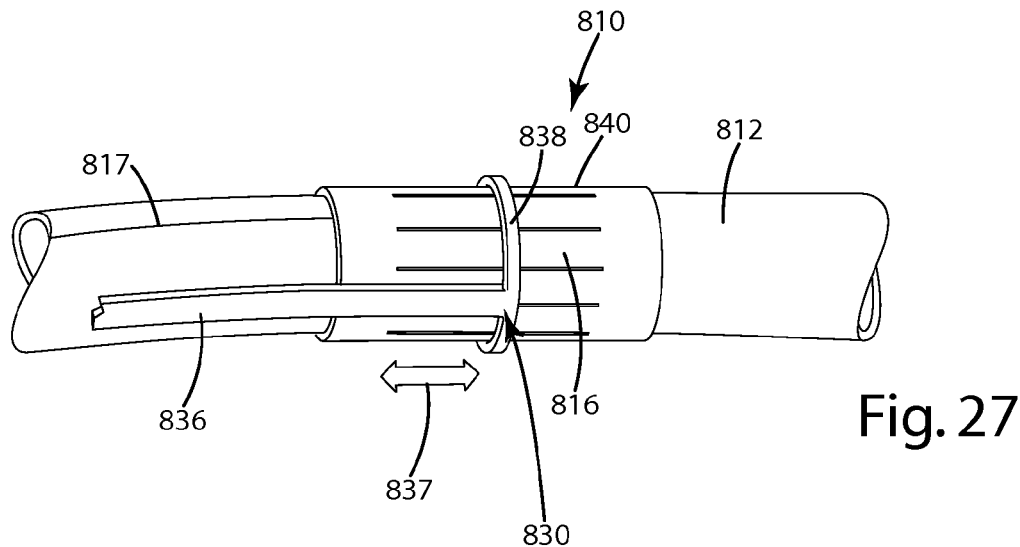
FIG. 27 is a perspective view of an eighth alternative embodiment of the device, including a sensor and another actuator, with the device in a retracted mode or first configuration.
Figure 28:
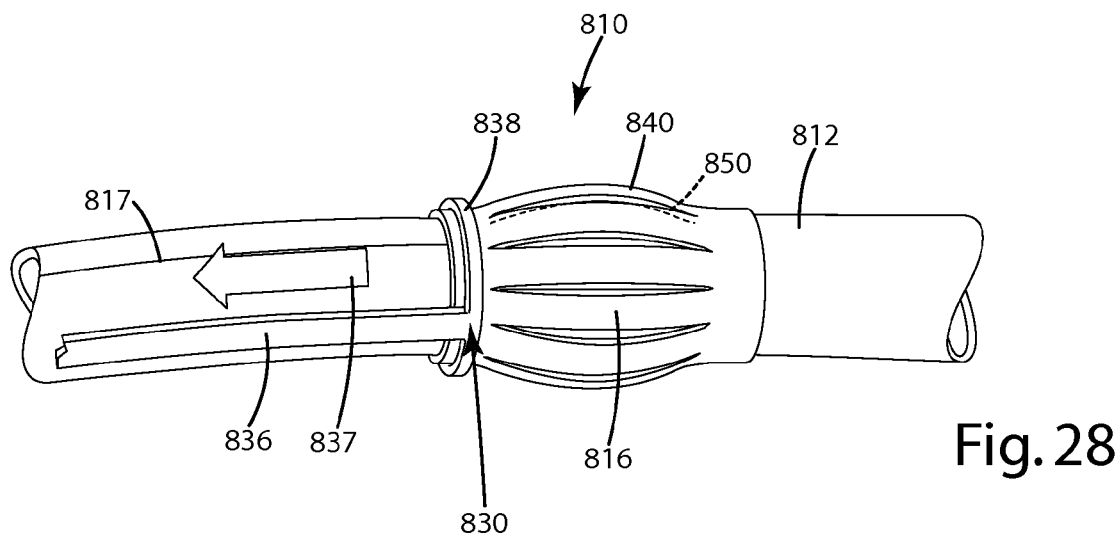
FIG. 28 is a perspective view of the eighth alternative embodiment of the device, including the support element, with the device in an extended mode or second configuration.

An eighth alternative embodiment of the device is shown in FIGS. 27 and 28 and generally designated 810. This embodiment is similar to the embodiments described above with several exceptions. For example, the actuator 830 of the device 810 can include a band or ring or tube 838 (all referred to as a "band" herein) that circumferentiates the multiple of strips 816 at a desired location. The band 838 can be joined with a force transmission element 836 that can be pulled or pushed by a healthcare provider while the device 810 is located within the desired laryngeal space. The force transmission element can be a flexible string-like element, or can be an elongate, semi-rigid or rigid element. By pulling or pushing on the band 838 with the force transmission element 836, the band is moved, relative to the plurality of strips 816, for example, by a sliding movement over the strips. The transmission element 836 can have a degree of movement sufficient to remove the band 838 from the strips 816. With the band removed, the strips 816 can be free to move.

Optionally, in this or other embodiments, each of the individual strips can be pre-formed in an arcuate configuration 850 as shown in FIG. 28. Accordingly, when the band 838 is removed from the strips 816, the strips will revert to the pre-formed arcuate configuration 850 and expand outwardly from a retracted mode as shown in FIG. 27 to the expanded mode as shown in FIG. 28. As a result, any sensors associated with the support element 816 can sufficiently engage the target muscle and/or nerve and operate as described in connection with the embodiments herein.

Where the force transmission element 836 is rigid or semi-rigid, it also can be adapted to slide the band 838 back over the multiple strips 816, returning the device 810 to the retracted mode as shown in FIG. 27.

The band 838 can be constructed from a variety of polymers, metals, composites, or combinations thereof. Optionally, the band can be constructed from a biocompatible, dissolvable material, which when placed in the laryngeal space begins to degrade. The particular material and the general thickness or dimension of the band 838 can be selected so that the band rapidly disintegrates or dissolves. The rate of disintegration or dissolving can be calibrated to a desired time frame so that after the device is adequately set in position in the laryngeal space (which should usually take no more than one to three minutes—and in many cases less than a minute), the band dissolves and releases the strips 816 so that the device 810 achieves the extended mode.

Figure 29:
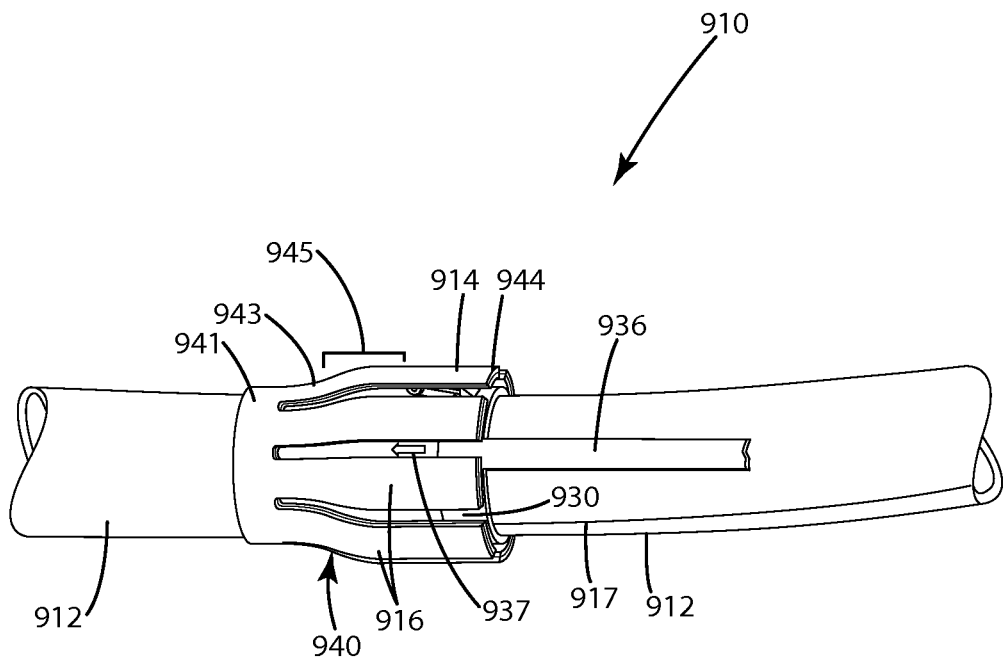
FIG. 29 is a perspective view of a ninth alternative embodiment of the device, including a support element, with the device in a retracted mode or first configuration.
Figure 30:
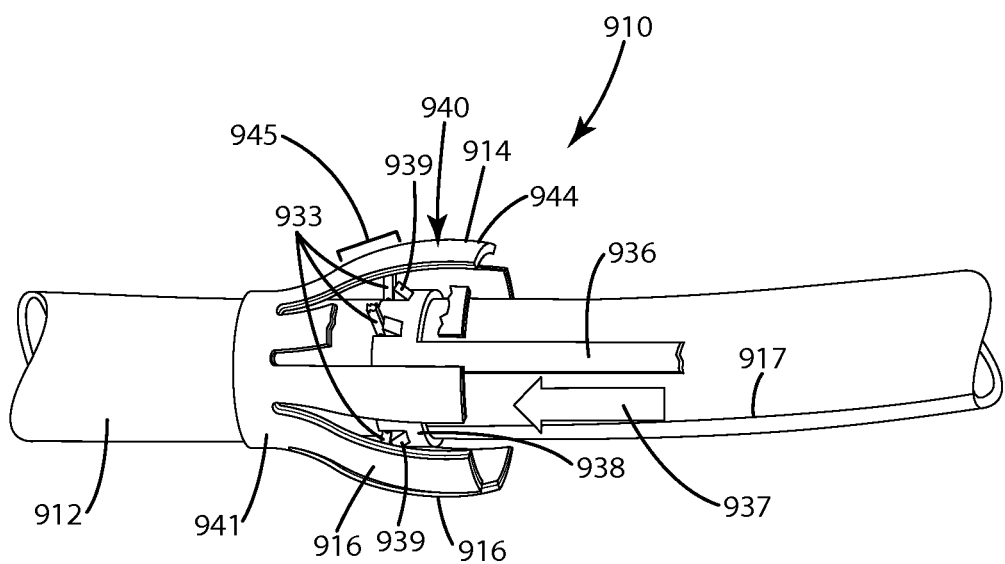
FIG. 30 is a perspective view of the ninth alternative embodiment of the device, including the support element, with the device in an expanded mode or second configuration.

A ninth alternative embodiment of the device is shown in FIGS. 29 and 30 and generally designated 910. This embodiment is similar to the embodiments above with several exceptions. For example, as shown in FIG. 29, this embodiment includes a support element 940 joined with an exteriorly located sensor 914 and an actuator 930 including a linking element 933 and a force transmission element 936. The support element 940 and/or sensor can be divided into multiple strips 916. These strips can be joined with connection element 941 at a first end 943 of the strips. The second end of the strips, however, 944 can be generally free. The actuator 930 can circumferentiate at least a portion of the cannula 912 and optionally can be disposed at least partially under one or more of the strips 916.

The linking element 933 can join the actuator 930 and a portion of one or more strips 916. For example, as illustrated in FIGS. 29-30, the linking elements 933 can join the actuator 930 with a central portion 945 of each of the strips 916. Each linking element 933 can be in the form of a single elongated, generally square member located between the actuator 930 and the respective strip. Optionally, the linking elements 933 can be in the form of a small wire frame that connects the actuator 930 and each of the strips. If desired, the ends of the linking elements 933 can include hinges to hingedly join the actuator and the respective strips. Further optionally, the linking elements 933 can be in the form of generally flexible elements that flex due to its physical or material properties. For example, the linking element can be constructed from a flexible polymer, or a metal strip of reduced central cross section.

The device, and more particularly the support element 916 can be converted from the retracted mode as shown in FIG. 29 to the expanded mode as shown in FIG. 30 by moving the force transmission element 936 in the direction of the arrow 937 in FIG. 30. This causes the linking element 933 to move and generally pivot outwardly, thereby exerting a force on the respective strip 916. This force causes at least central portions 945, and optionally the free ends 944, of the strips to move generally outwardly away from the cannula 912. This movement may be generally radially outward or in some other movement, away from the cannula 912. The movement can continue until the linking element 933 effectively locks in a desired position, or can continue until the operator ceases movement of the force transmission member 936.

In the extended configuration of FIG. 30, the free ends 944 can be suspended a distance away from the cannula 912. This distance can be selected so that the free ends do not unacceptably traumatize tissue in the laryngeal space or other internal body space. Further, the free ends 944 can be configured so that they are generally arcuate, and round and extend back toward the cannula 912, even when in the extended mode.

Optionally, the actuator 930 can include one or more respective locking tabs 939. These tabs can limit the amount of rotational movement of the linking elements 933 so that when the actuator 933 is moved a sufficient distance forward, the linking elements simply fall back against the locking tabs 939, and the strips remain in the extended mode as shown in the extended mode in FIG. 30.

In the extended mode, the sensors 914 on the support element can operate to monitor target laryngeal muscles or nerves or other target muscles or nerves as in the embodiments described above.

The various components, features and/or elements of the embodiments described herein can be interchanged in a variety of configurations to yield a variety of products. Any of the embodiments herein can include, in whole or in part, components, features and/or elements mentioned of any other embodiments described herein.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The invention claimed is:

1. A nerve monitoring device comprising:
a support element joined with a plurality of sensors and arranged to join a tube, the support element including a plurality of strips oriented generally parallel to the longitudinal axis of a tube, each strip having a strip sensor, the plurality of strips joined with a first connection element that at least partially surrounds a tube, the strips moveable between a retracted mode, in which the strips are positioned adjacent a tube, and an extended mode, in which at least a portion of the strips extend outwardly from a tube so that the strips conform to the anatomical geometry of at least a portion of a space of a subject in an atraumatic manner;
wherein two or more of the strips are placed immediately adjacent to each other so that the strips provide sufficient circumferential coverage such that rotational orientation does not affect the monitoring of at least one nerve; and
wherein at least one of the sensors is adapted to measure the activity of at least one nerve when placed in monitoring proximity so that a health care provider can be provided with information concerning the location of a nerve.

2. The device of claim 1 comprising:
an endotracheal tube configured for insertion into a laryngeal space of a subject, the endotracheal tube including a longitudinal axis;
the sensors joined with the endotracheal tube at a predetermined location corresponding to at least one of a target laryngeal muscle and a laryngeal nerve when the endotracheal tube is positioned through a glottic opening of the subject; and
an output element in communication with at least one of the sensor, the output element providing output indicative of measured activity of at least one of the target laryngeal muscle and the laryngeal nerve when a probe is positioned adjacent or on the laryngeal nerve;
wherein the support element includes a second connection element joined with the plurality of strips distal from the first connection element, wherein each of the plurality of strips are located between and joined with both the first connection element and the second connection element, wherein the second connection element is moveable toward the first connection element.

3. The device of claim 2 wherein each of the plurality of strips include a first end joined with the first connection element, a second end joined with the second connection element, and a central portion located between the first end and the second end.

4. The device of claim 3 wherein the central portion moves away from the endotracheal tube a greater distance then the first end moves away from the endotracheal tube when the strips are in the extended mode.

5. The device of claim 1 wherein the plurality of strips are flexible, and wherein the plurality of strips include a portion that bends outwardly to a generally convex configuration when the strips are moved from the retracted mode to the extended mode.

6. The device of claim 5 wherein the strips are formed in an accurate shape, wherein a band holds the strips in a linear shape in the retracted mode.

7. The device of claim 1 wherein the support element is joined with the sensors so that at least one of the sensors is located on an exterior of the support element and adapted to a nerve.

8. A laryngeal nerve monitoring device comprising:
an endotracheal tube configured for insertion into a laryngeal space of a subject, the endotracheal tube including a longitudinal axis;
a sensor joined with the endotracheal tube at a predetermined location corresponding to at least one of a target laryngeal muscle and a laryngeal nerve when the endotracheal tube is positioned through the glottic opening of the subject, a plurality of strips oriented generally parallel with the longitudinal axis of the endotracheal tube, the plurality of strips joined with a first connection element that at least partially surrounds the endotracheal tube, the strips moveable between a retracted mode, in which the strips are positioned adjacent the endotracheal tube, and an extended mode, in which at least portions of the strips are spaced outwardly a preselected distance from the endotracheal tube so that the strips conform to the anatomical geometry of at least a portion of the laryngeal space of the subject in an atraumatic manner; and
an output element in communication with the sensor, the output element providing output indicative of measured activity of at least one of the target laryngeal muscle and the laryngeal nerve when a probe is positioned adjacent or on the laryngeal nerve; and
an actuator joined with the sensor, the actuator adapted to engage at least one of the plurality of strips and the first connection element, the actuator adapted to enable the strips to move from the retracted mode to the extended mode,
wherein two or more of the strips are placed immediately adjacent to each other so that the sensor provides sufficient circumferential coverage such that it is placed in monitoring proximity to at least one of the laryngeal muscle and laryngeal nerve, and
wherein the sensor is adapted to measure the activity of the at least one of the target laryngeal muscle and the laryngeal nerve when placed in monitoring proximity to the at least one of the target laryngeal muscle and the laryngeal nerve, so that a health care provider can be provided with information concerning the location of the laryngeal nerve.

9. The device of claim 8 wherein the actuator is in the form of a band that circumferentiates the plurality of strips, wherein the band is moveable relative to the strips toward the first connection element.

10. A nerve monitoring device comprising:
a cannula configured for insertion into an internal body space of a subject, the cannula including a longitudinal axis;
a sensor joined with the cannula at a predetermined location, the predetermined location corresponding to at least one of a target muscle and a target nerve when the cannula is positioned in the internal body space of the subject;
a support element joined with a plurality of the sensors and the cannula, the support element including a plurality of strips, each strip having a strip sensor, the plurality of strips moveable between a retracted mode, in which the strips are positioned adjacent the cannula, and an extended mode, in which at least portions of the strips are spaced outwardly a preselected distance from the cannula so that the strips conform to the anatomical geometry of at least a portion of the internal body space of the subject in an atraumatic manner; and an actuator joined with the support element, the actuator adapted to engage at least one of the plurality of strips so that the strips move from the retracted mode to the extended mode,
wherein two or more of the strips are placed immediately adjacent to each other so that the strips provide sufficient circumferential coverage such that under any orientation, at least one strip sensor is placed in monitoring proximity to at least one nerve; and
wherein the sensor is adapted to measure the activity of the at least one of the target muscle and the target nerve when placed in electrical proximity to the at least one of the target muscle and target nerve, so that a health care provider can be provided with information concerning the location of the target nerve so as to avoid unwanted damage or impairment thereto.

11. The device of claim 10 wherein the plurality of strips bend outwardly to a convex configuration in the extended mode.

12. The device of claim 10, further comprising a second connection element spaced from the first connection element, wherein the first connection element moves toward the second connection element when the support element transitions from the retracted mode to the extended mode.

13. The device of claim 12 wherein the first and second connection elements each are in a tubular form, the tubular form at least partially surrounding the cannula, wherein the first connection element is slidable along the cannula.

14. The device of claim 10 wherein the actuator includes a linking element that extends toward and is joined with at least one of the plurality of strips, wherein the at least one of the plurality of strips includes a first end and a second end and a central portion therebetween, wherein the first connection element is joined with the at least one of the plurality of strips at the first end, wherein the linking element is joined with the at least one of the plurality of strips in the central portion.

15. A laryngeal nerve monitoring device comprising:
a cannula configured for insertion into an internal body space of a subject, the cannula including a longitudinal axis;
a sensor joined with the cannula at a predetermined location corresponding to at least one of a target muscle and a target nerve when the cannula is positioned at least partially in the internal body space, the sensor including a plurality of strips oriented generally parallel with the longitudinal axis of the cannula, the plurality of strips joined with a first connection element, the strips moveable between a retracted mode, in which the strips are positioned adjacent the cannula, and an extended mode, in which the strips project outwardly a preselected distance from the cannula so that the strips conform to the anatomical geometry of at least a portion of the internal body space of the subject in an atraumatic manner; and an actuator joined with the sensor, the actuator adapted to engage at least one of the plurality of strips and the first connection element, the actuator adapted to enable the strips to move from the retracted mode to the extended mode, wherein a support element comprises a plurality of sensors, one or more arranged on each of the plurality of strips, with two or more of the strips placed immediately adjacent to each other to provide sufficient circumferential coverage such that at least one sensor is placed in monitoring proximity to at least one of the laryngeal muscle and laryngeal nerve without regard to the rotational orientation of the support element, and wherein the sensor is adapted to measure the activity of the at least one of the target muscle and the target nerve when placed in monitoring proximity to the at least one of the target muscle and the target nerve, whereby a health care provider is provided with information concerning the location of the target nerve.

16. The device of claim 15 wherein the strips include a plurality of electrodes in an array circumferentially disposed around an outer circumference of the cannula, the array configured so that at least two of the electrodes can be in electrical contact with the at least one of the target muscle and target nerve regardless of the rotational orientation of the cannula within the internal body space when the sensor is in the extended mode.

* * * * *